(12) United States Patent
Dijk et al.

(10) Patent No.: US 8,285,382 B2
(45) Date of Patent: Oct. 9, 2012

(54) DETERMINING STIMULATION SIGNALS FOR NEURAL STIMULATION

(75) Inventors: Bastiaan van Dijk, Mechelen (BE); Matthijs Killian, Mechelen (BE); Andreas Buechner, Isemhagen (DE); Joerg Pesch, Hannover (DE); Marc Majoral, Brussels (BE); John L. Parker, Roseville (AU); James F. Patrick, Roseville (AU); Ernst von Wallenberg, Muelheim (DE)

(73) Assignee: Cochlear Limited, Macquarie University, NSW (AU)

( * ) Notice: Subject to any disclaimer, the term of this patent is extended or adjusted under 35 U.S.C. 154(b) by 1539 days.

(21) Appl. No.: 11/451,349

(22) Filed: Jun. 13, 2006

(65) Prior Publication Data

US 2006/0235490 A1 Oct. 19, 2006

Related U.S. Application Data

(63) Continuation-in-part of application No. 11/094,769, filed on Mar. 31, 2005, now Pat. No. 7,822,478, which is a continuation-in-part of application No. 10/343,397, filed as application No. PCT/AU01/01032 on Aug. 21, 2001, now Pat. No. 7,272,446.

(60) Provisional application No. 60/557,675, filed on Mar. 31, 2004, provisional application No. 60/616,216, filed on Oct. 7, 2004.

(51) Int. Cl.
*A61N 1/36* (2006.01)

(52) U.S. Cl. .......................................................... 607/55

(58) Field of Classification Search .............. 607/55–57, 607/136–137; 600/25; 381/312
See application file for complete search history.

(56) References Cited

U.S. PATENT DOCUMENTS

| 4,352,930 A | | 10/1982 | Chance |
| 4,441,202 A | * | 4/1984 | Tong et al. .................... 381/326 |
| 4,515,158 A | * | 5/1985 | Patrick et al. .................. 607/57 |
| 4,532,930 A | | 8/1985 | Crosby et al. |
| 4,611,596 A | * | 9/1986 | Wasserman .................... 607/57 |
| 4,847,617 A | | 7/1989 | Silvian |
| 5,046,242 A | | 9/1991 | Kuzma |
| 5,271,397 A | | 12/1993 | Seligman et al. |

(Continued)

FOREIGN PATENT DOCUMENTS

AU 2005202733 A1 1/2006

(Continued)

OTHER PUBLICATIONS

Bernd Edler, Heiko Purnhagen, and Charalampos Ferekidis, ASAC—Analysis/Synthesis Audio Codec for Very Low Bill Rates, 100th AES Convention, Copenhagen (May 1996).

(Continued)

*Primary Examiner* — Carl H Layno
*Assistant Examiner* — Roland Dinga
(74) *Attorney, Agent, or Firm* — Kilpatrick, Townsend & Stockton, LLP.

(57) ABSTRACT

An embodiment of the present invention takes masking effects into consideration when determining stimulation signals for neural stimulation. These masking effects may be modeled using user-specific models determined by taking measurements for an implant system of an implant recipient. Or, the model may correspond to a group of individuals sharing a common characteristic or the population as a whole. These models may be, for example, psycho-physical models.

20 Claims, 13 Drawing Sheets

U.S. PATENT DOCUMENTS

| | | | |
|---|---|---|---|
| 5,274,711 A * | 12/1993 | Rutledge et al. | 704/225 |
| 5,403,262 A * | 4/1995 | Gooch | 600/28 |
| 5,412,748 A | 5/1995 | Furuyama et al. | |
| 5,601,617 A | 2/1997 | Loeb et al. | |
| 5,609,616 A | 3/1997 | Schulman et al. | |
| 5,626,629 A | 5/1997 | Faltys et al. | |
| 5,649,970 A | 7/1997 | Loeb et al. | |
| 5,653,742 A | 8/1997 | Parker et al. | |
| 5,687,282 A * | 11/1997 | Van De Kerkhof | 704/205 |
| 5,776,179 A * | 7/1998 | Ren et al. | 607/137 |
| 5,786,439 A | 7/1998 | Van Antwerp et al. | |
| 5,824,022 A * | 10/1998 | Zilberman et al. | 607/57 |
| 5,833,714 A | 11/1998 | Loeb | |
| 5,853,424 A | 12/1998 | Rise | |
| 5,895,416 A | 4/1999 | Barreras, Sr. et al. | |
| 5,909,497 A | 6/1999 | Alexandrescu | |
| 6,115,478 A | 9/2000 | Schneider | |
| 6,116,413 A | 9/2000 | Tabor et al. | |
| 6,198,971 B1 | 3/2001 | Leysieffer | |
| 6,230,057 B1 | 5/2001 | Chow et al. | |
| 6,231,126 B1 | 5/2001 | Cheng | |
| 6,304,786 B1 | 10/2001 | Heil, Jr. et al. | |
| 6,304,787 B1 | 10/2001 | Kuzma et al. | |
| 6,321,126 B1 | 11/2001 | Kuzma | |
| 6,334,072 B1 | 12/2001 | Leysieffer | |
| 6,354,299 B1 | 3/2002 | Fischell et al. | |
| 6,366,863 B1 | 4/2002 | Bye et al. | |
| 6,421,569 B1 | 7/2002 | Treaba et al. | |
| 6,463,328 B1 | 10/2002 | John | |
| 6,497,729 B1 | 12/2002 | Moussy et al. | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,594,525 B1 | 7/2003 | Zierhofer | |
| 6,697,674 B2 | 2/2004 | Leysieffer et al. | |
| 6,751,505 B1 | 6/2004 | Van Den Honert et al. | |
| 6,778,040 B2 | 8/2004 | Kim | |
| 6,778,858 B1 * | 8/2004 | Peeters | 607/57 |
| 6,879,693 B2 | 4/2005 | Miller et al. | |
| 6,916,291 B2 | 7/2005 | Givens et al. | |
| 7,171,272 B2 | 1/2007 | Blamey et al. | |
| 7,181,297 B1 | 2/2007 | Pluvinage et al. | |
| 7,218,971 B2 | 5/2007 | Heil, Jr. et al. | |
| 7,251,530 B1 | 7/2007 | Overstreet et al. | |
| 7,272,446 B2 | 9/2007 | Parker et al. | |
| 7,317,944 B1 | 1/2008 | Overstreet | |
| 7,328,151 B2 | 2/2008 | Muesch | |
| 7,822,478 B2 | 10/2010 | Killian et al. | |
| 2001/0050837 A1 | 12/2001 | Stevenson et al. | |
| 2002/0176584 A1 | 11/2002 | Kates | |
| 2003/0109903 A1 | 6/2003 | Berrang et al. | |
| 2003/0199950 A1 | 10/2003 | Stolz et al. | |
| 2003/0233133 A1 | 12/2003 | Greenberg et al. | |
| 2004/0098063 A1 | 5/2004 | Goetz | |
| 2004/0127968 A1 | 7/2004 | Kuzma et al. | |
| 2004/0147992 A1 | 7/2004 | Bluger et al. | |
| 2006/0004432 A1 | 1/2006 | Parker et al. | |
| 2007/0127745 A1 | 6/2007 | Gibson et al. | |
| 2008/0051853 A1 | 2/2008 | Parker et al. | |
| 2009/0177247 A1 | 7/2009 | Neal et al. | |
| 2009/0204177 A1 | 8/2009 | Parker et al. | |
| 2009/0292161 A1 | 11/2009 | Parker | |

FOREIGN PATENT DOCUMENTS

| | | |
|---|---|---|
| EP | 0247649 | 12/1987 |
| EP | 0282336 | 9/1988 |
| EP | 0 124 930 B1 | 6/1990 |
| JP | 61001200 | 1/1986 |
| JP | 63242252 | 10/1988 |
| JP | 8501241 | 2/1996 |
| JP | 10508442 | 8/1998 |
| JP | 11-513539 T | 11/1999 |
| JP | 2000509566 | 7/2000 |
| WO | 9324176 | 12/1993 |
| WO | 9501709 | 1/1995 |
| WO | 9612383 | 4/1996 |
| WO | WO 96/26673 A1 | 9/1996 |
| WO | 9709863 A1 | 3/1997 |
| WO | 97/43871 A1 | 11/1997 |
| WO | 97/48447 | 12/1997 |
| WO | 9965276 | 12/1999 |
| WO | 0103622 | 1/2001 |
| WO | 0119304 | 3/2001 |
| WO | WO01/19304 A1 * | 3/2001 |
| WO | 0199470 | 12/2001 |
| WO | WO 02/17679 A1 | 2/2002 |

OTHER PUBLICATIONS

Frank Baumgarte, Charalampos Ferekidis, and Hendrik Fuchs, A Nonlinear Psychoacoustic Model Applied to the ISO MPEG Layer 3 Coder, 99th AES Convention, New York (Oct. 1995).

Lawrence T. Cohen, Louise M. Richards, Elaine Saunders, and Robert S.C. Cowen, Spatial Spread of Neural Excitation in Cochlear Implant Recipients: Comparison of Improved ECAP Method and Psychophysical Forward Masking, 179 Hearing Res. 72-87 (May 2003).

Abbas PJ, Brown CJ, Hughes ML, Ganz BJ, Wolaver AA, Gervais JP and Hong SH, Electrically evoked compound action potentials recorded from subjects who use the nucleus C124M device, 185 Ann Otol Rhinol Laryngol Suppl. 6-9 (Dec. 2000).

Lawrence T. Cohen, Elaine Saunders, and Louise M. Richardson, Spatial Spread of Neural Excitation: Comparison of Compund Action Potential and Forward-Masking Data in Cochlear Implant Recipients, 43 International Journal of Audiology.

Miller CA, Abbas PJ, Brown CJ, An Improved Method of Reducing Stimulus Artifact in the Electrically Evoked Whole Nerve Potential 21(4) Ear Hear 280-90 (Aug. 2000).

International Search Report dated Oct. 5, 2001; counterpart patent application PCT/AU01/01032 filed Aug. 21, 2001; Publication No. WO 02/17679; Publication Date Feb. 28, 2002: Inventors: John Parker et al.: Applicant Cochlear Limited.

International Preliminary Examination Report dated Apr. 10, 2002; counterpart patent application PCT/AU01/01032 filed Aug. 21, 2001; Publication No. WO 02/17679; Publication Date Feb. 28, 2002: Inventors: John Parker et al.: Applicant Cochlear Limited.

Supplemental European Search Report dated Aug. 11, 2005.

CA Examiner's report dated May 29, 2007.

Nogueira et al. "A Psychoacoustic 'NofM'—Type Speech Coding Strategy for Cochlear Implants," EURASIP Journal on Applied Signal Processing, pp. 3044-3059, 2005.

Supplementary European Search Report dated Aug. 11, 2005.

First European Examiner's Report for European Application No. 01959971.1 dated dated Nov. 23, 2005.

Second CA Office Action dated Dec. 10, 2008.

Japanese Patent Application No. 2002-561453, Notice of Reasons for Rejection dated Jun. 16, 2009. (English Translation).

Final Office Action issued in U.S. Appl. No. 11/857,253, mailed Mar. 17, 2011. (10 Pages).

SCS, Specialty Coating Systems: Rubber/Silicone, Retrieved on Nov. 24, 2005 (based on records of Internet Archive), Webpage available on: www.scscoatings.com/.

U.S. Appl. No. 10/343,397, Notice of Allowance mailed on Feb. 12, 2007, 6 Pages.

U.S. Appl. No. 10/343,397, Office Action mailed on Aug. 30, 2006, 9 Pages.

U.S. Appl. No. 10/343,397, Office Action mailed on Feb. 8, 2006, 9 Pages.

U.S. Appl. No. 10/343,397, Notice of Allowance mailed on May 9, 2007, 6 Pages.

U.S. Appl. No. 11/094,769, Notice of Allowance mailed on Jun. 16, 2010, 7 Pages.

U.S. Appl. No. 11/094,769, Notice of Allowance mailed on Jan. 14, 2010, 8 Pages.

U.S. Appl. No. 11/094,769, Notice of Allowance mailed on Mar. 25, 2009, 6 Pages.

U.S. Appl. No. 11/094,769, Office Action mailed on Jul. 21, 2008, 10 Pages.

U.S. Appl. No. 11/094,769, Office Action mailed on Jun. 10, 2009, 8 Pages.

U.S. Appl. No. 11/857,253, Office Action mailed on Mar. 29, 2010, 19 Pages.

U.S. Appl. No. 11/857,253, Office Action mailed on Oct. 7, 2010, 9 Pages.

Bernd Edler, Heiko Purnhagen, and Charalampos Ferekidis, *ASAC—Analysis/Synthesis Audio Codec for Very Low Bit Rates*, 100th AES Convention, Copenhagen (May 1996).

Abbas PJ, Brown CJ, Hughes ML, Ganz BJ, Wolaver AA, Gervais JP and Hong SH, *Electrically evoked compound action potentials recorded from subjects who use the nucleus CI24M device*, 185 Ann Otol Rhinol Laryngol Suppl. 6-9 (Dec. 2000).

Lawrence T. Cohen, Elaine Saunders, and Louise M. Richardson, *Spatial Spread of Neural Excitation: Comparison of Compound Action Potential and Forward-Masking Data in Cochlear Implant Recipients*, 43 International Journal of Audiology 346-355 (2004).

Miller CA, Abbas PJ, Brown CJ, *An Improved Method of Reducing Stimulus Artifact in the Electrically Evoked Whole Nerve Potential*, 21(4) Ear Hear 280-90 (Aug. 2000).

\* cited by examiner

DETERMINING STIMULATION SIGNALS FOR NEURAL STIMULATION

CROSS-REFERENCE TO RELATED APPLICATIONS

This application is a continuation-in-part of U.S. application Pat No. 7,822,478, filed Mar. 31, 2005, entitled "Compressed Neural Coding," now pending, which is a continuation-in-part of Pat. No. 7,272,446, filed Feb. 21, 2003, entitled "Power Efficient Electrical Stimulation," which is a national stage of PCT application PCT/AU01/01032, filed Aug. 21, 2001, which claims priority to Australian Patent Application No. PQ9528 filed Aug. 21, 2000. This application also claims the benefit of the following U.S. provisional applications: U.S. Provisional Application No. 60/557,675, entitled "Spread of Excitation and MP3 Coding," filed Mar. 31, 2004; and U.S. Provisional Application No. 60/616,216, entitled "Spread of Execution and Compressed Audible Speech Coding," filed Oct. 7, 2004. The above applications are hereby incorporated by reference herein.

This application also makes reference to the following co-pending U.S. Patent Applications: U.S. application Ser. No. 10/478,675, entitled "A Peak-Derived Timing Stimulation Strategy for a Multi-Channel Cochlear Implant," filed Nov. 24, 2003; U.S. Application No. 60/548,104, entitled "Rotable Belt Clip for Body-Worn Speech Processor," filed Feb. 27, 2004; U.S. Application No. 60/548,094, entitled "Reversible Belt Clip for Body-Worn Speech Processor," filed Feb. 27, 2004; U.S. application Ser. No. 10/798,847, entitled "Virtual Wire Assembly having Hermetic Feedthroughs," filed Mar. 12, 2004; and U.S. Application No. 60/557,713 "Ramping Pulse Train Stimulation," filed Mar. 31, 2004. The above applications are hereby incorporated by reference herein.

BACKGROUND

1. Field of the Invention

The present invention relates generally to neural stimulation, and more particularly, to determining stimulation signals for neural stimulation.

2. Related Art

Wearable medical devices reliant upon stored power share a common dynamic. As the possible and desired functionality of the devices is improved, the power demands generally increase. As a result, the life per charge or per battery cell is reduced. This not only raises costs for the user (also referred to herein as the patient, wearer and recipient; collectively and generally referred to herein as "recipient"), it also increases the risk that a device will cease operating at an inconvenient time due to loss of power.

In the field of prosthetic hearing devices such as cochlear™ implants (also commonly referred to as cochlear™ implant devices, cochlear™ prostheses, and the like; simply "cochlear implant" herein), these concerns are exacerbated by the trend toward a single, behind-the-ear (BTE) unit to replace what was once a head mounted unit and a separate speech processor unit worn on the recipient's body. The available volume and weight which may be allocated to a power source is accordingly reduced. Increased power demand to provide improved functionality creates a need to consider the efficiency of speech processing schemes and stimulus sets in order to provide maximum battery life.

SUMMARY

In one aspect of the invention, a method of providing neural stimulation to a recipient is disclosed. The method comprises: receiving an acoustical signal; determining a set of stimulation signals based on the received acoustical signal, comprising: determining a first stimulation signal based on a perceptual power of the first stimulation signal; and determining at least one other stimulation signal based on a perceptual power of the at least one other stimulation signal using information indicative of a masking effect of the first stimulation signal on the at least one other stimulation signal; and applying stimuli to a recipient using the determined stimulation signals.

In another aspect of the invention, a system for neural stimulation is disclosed. The system comprises: a microphone capable of receiving an acoustical signal; a speech processing unit capable of determining a set of stimulation signals based on the received acoustical signal; and an implant capable of applying stimuli to a recipient using the determined stimulation signals; wherein the speech processing unit in determining the set of stimulation signal is further capable of determining a first stimulation signal based on a perceptual power of the first stimulation signal, and determining at least one other stimulation signal based on a perceptual power of the at least one other stimulation signal using information indicative of a masking effect of the first stimulation signal on the at least one other stimulation signal.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Figure 1:
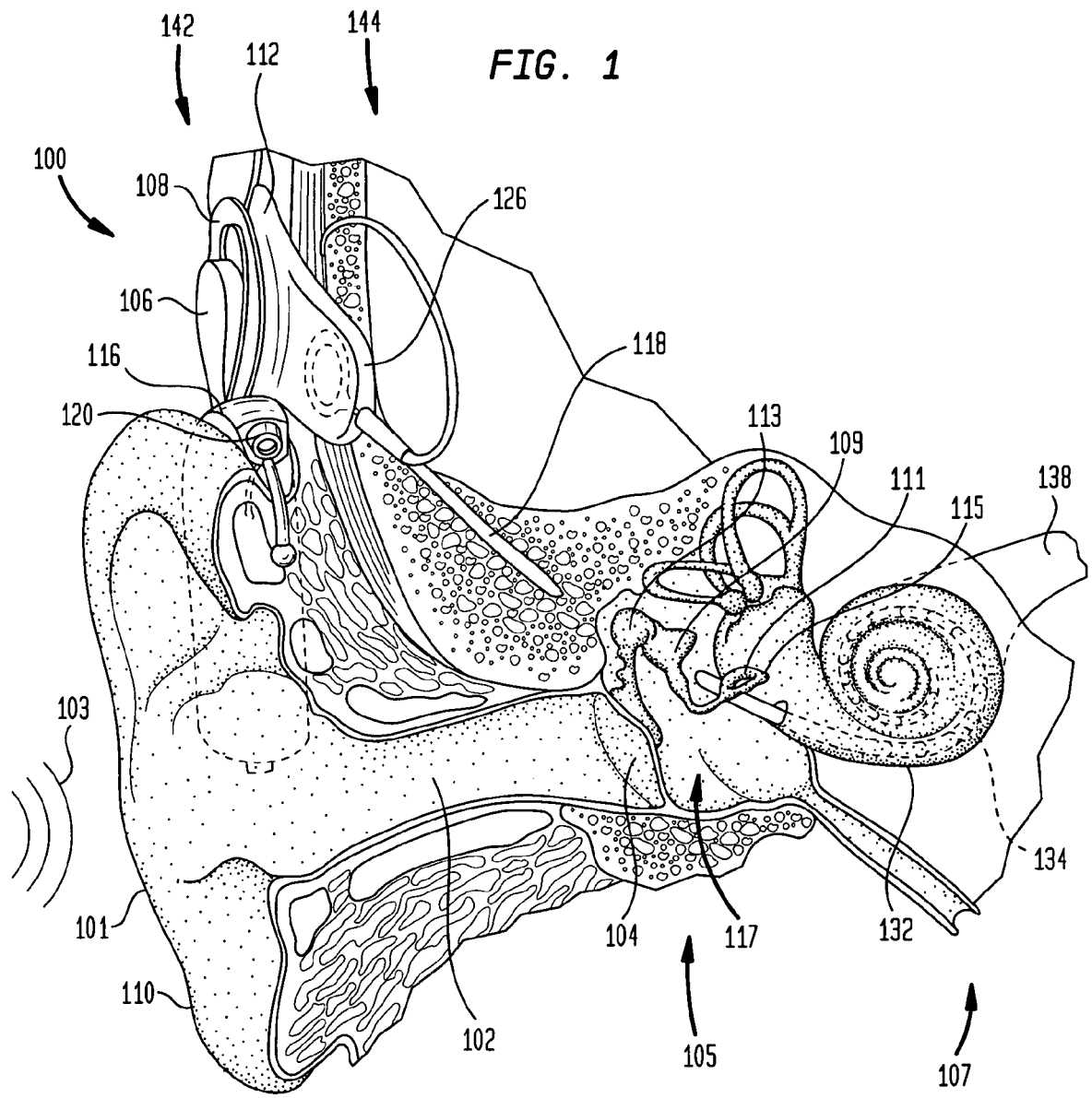
FIG. 1 is a schematic block diagram of one embodiment of an exemplary prosthetic hearing device, a cochlear implant, suitable for implementing embodiments of the present invention.

Embodiments of the present invention are described herein primarily in connection with one type of stimulating medical device, a prosthetic hearing implant system. Prosthetic hearing implant systems include but are not limited to hearing aids, auditory brain stimulators, cochlear prostheses and the like. Cochlear prostheses, also referred to as cochlear implants, use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem, typically with an electrode array in which the electrode contacts are disposed on a two dimensional surface that can be positioned proximal to the brainstem. FIG. 1 is a perspective view of a cochlear implant in which the effective width of the electrodes may be adjusted in accordance with the teachings of the present invention.

FIG. 1 is a perspective view of an exemplary cochlear implant system in which the present invention may be implemented. The relevant components of outer ear 101, middle ear 105 and inner ear 107 are described next below. An acoustic pressure or sound wave 103 is collected by outer ear 101 (e.g., the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient. External assembly 142 typically comprises microphone 120 for detecting sound, a speech processing unit 116, a power source (not shown), and an external transmitter unit 106. External transmitter unit 106 comprises an external coil 108 and, preferably, a magnet (not shown) secured directly or indirectly to the external coil 108. Speech processing unit 116 processes the output of microphone 120 that is positioned, in the depicted embodiment, by ear 110 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it can fit behind outer ear 101 (e.g., the auricle). Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes. Signals generated by stimulator unit 126 are applied by the electrodes of electrode array 134 to cochlea 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to ear 110 of the recipient.

Further details of the above and other exemplary prosthetic hearing implant systems in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein in their entireties. For example, while cochlear prosthesis 100 is described as having external components, in alternative embodiments, cochlear prosthesis 100 may be a totally implantable prosthesis. In one exemplary implementation, for example, speech processing unit 116, including the microphone, speech processor and/or power supply may be implemented as one or more implantable components. In one particular embodiment, speech processing unit 116 may be contained within the hermetically sealed housing used for speech processing unit 116.

In both normal hearing as well as in hearing as a response to electrical stimulation (electrical hearing) the presence of a signal can prevent or change the detection of other signals that are also present in the spectrum, this effect is called masking. The masking phenomena may be estimated using various models, such as psychoacoustical masking models (for estimation of the masking effects in normal hearing) and psychoelectric masking models (to estimate the masking effect in electric hearing).

In certain embodiments of the present invention, the cochlear prosthesis utilizes these estimated masking effects when determining the characteristics of the stimulation signals that will be applied to auditory nerve 138. This allows speech processing unit 116 to select stimulation signals having greater, and preferably the highest, perceptual power, rather than selecting stimulation signals having the highest spectral power, when selecting the signals for stimulating auditory nerve 138. The following provides a more detailed description of methods and systems for utilizing estimated masking effects of the stimulation signals when selecting the stimulation signals to be applied to auditory nerve 138.

For ease of discussion, we will use the following two terms in the following discussion: spectral power, and perceptual power. Classically, if we decompose a complex sound into frequency bands or channels we can compare the relative 'importance' of each band by looking at the relative physical amplitudes in terms of, for example, sound pressure level. As noted, we will refer to this relative physical amplitude as the "spectral power" of the frequency band. This method of selecting maxima based on highest spectral powers is currently used in current speech processing strategies for commercially available cochlear implants such as Speak and ACE. Since spectral power is purely a physical measure, it does not take into account actual perception. For example, a tone that is above the maximum audible frequency may have very high spectral power but still be inaudible and thus will not be perceived by an normal hearing listener. To identify how important a frequency component is for the perception of the sound, the term 'perceptual power' is used herein to refer to the actual contribution of that component to perception. For example, the tone mentioned above that is outside the audible frequency range may have high spectral power but will have no perceptual power.

In one embodiment, the cochlear prosthesis uses a psychophysical model such as, for example, a psychoacoustic model or a psychoelectric model. Each of these comprises mathematical models of the masking properties of the human auditory system. A psychoelectric model is concerned with electrical stimuli (e.g., pulse bursts) on electrodes, while a psychoacoustical model relates to acoustical stimulation of the normal ear. As used herein, the term psychoelectric model refers to any model concerned with electrical stimuli of electrodes, including both user-specific models and models for a population of implant recipients, including for example, all implant recipients or a population of implant recipients sharing a common characteristic. In some embodiments, the psychoelectrical model may be very complicated and may model many explicit characteristic of the electrically stimulated auditory nerve. Or, in other embodiments, the psychoelectrical model may be a very simple scheme, such as, one wherein electrodes neighboring the masking electrode are automatically deemed masked and, accordingly, not stimulated.

This simplified scheme is referred to as an N+X scheme, where X represents the number of neighboring electrodes that are to be deemed masked and, accordingly, not stimulated. For example, an N+1 scheme would result in the electrodes immediately on either side of the electrode automatically being excluded from consideration as electrodes for application of stimuli. Or, an N+2 scheme would result in the 2 electrodes closest to the select electrode on either side being considered as automatically masked.

The term "psychoacoustic model" as used herein refers to a model that models a population of normal hearing persons. This population may be, for example, for all normal hearing persons as a whole, or for a group of persons, sharing a common characteristic (e.g., elderly persons with reduced hearing, children, females, etc.). Exemplary psychoacoustic models include, for example, the MPEG-1 Psychoacoustic Model 1, and the MPEG-2 Psychoacoustic Model 2.

A more detailed description of exemplary psychoacoustic models can be found in Bernd Edler, Heiko Purnhagen, and Charalampos Ferekidis, *ASAC—Analysis/Synthesis Audio Codec for Very Low Bit Rates,* 100th AES Convention, Copenhagen (May 1996); and Frank Baumgarte, Charalampos Ferekidis, and Hendrik Fuchs, *A Nonlinear Psychoacoustic Model Applied to the ISO MPEG Layer 3 Coder,* 99th AES Convention, New York, October 1995 (hereinafter "the Baumgarte reference"), both of which are hereby incorporated by reference herein.

It is noted that masking models may be expressed in sound intensity (dB) vs frequency or in stimulating current vs electrode number or channel number. These different representations of the same thing can be interchanged and calculated from one to another and back. It will be clear to somebody skilled in the art that this transformation arises uniquely from the processing path used. For ease in explanation, the term "tonal psychoelectric model" is used herein to refer to a psychoelectric model that is in terms of sound pressure level (for example, in terms of decibels (dB) or decibel volts (dBV)) versus frequency (e.g., in terms of Hertz (Hz)). That is, a tonal psychoelectric model is a model that is concerned with electrical stimuli of electrodes, but is in terms of sound pressure level (e.g., dB or dBV) versus frequency (Hz) as opposed to microvolts (or current level) versus electrode number. In a cochlear prosthesis such as cochlear prosthesis 100 described above, the individual or combinations of neighboring electrodes of electrode array 134 correspond to different frequency bands, and as such, in principal a psychoelectric model can be translated into a tonal psychoelectric model, and visa versa. That is, there is a one-to-one relationship between stimulation current on a specific electrode and acoustical energy present in the spectral band belonging to this electrode. For clarity, the term "psychoelectric model"

will be used hereinafter to refer to both psychoelectric models in terms of intensity (e.g., microvolts or current level) versus electrode as well as tonal psychoelectric models.

Figure 2:
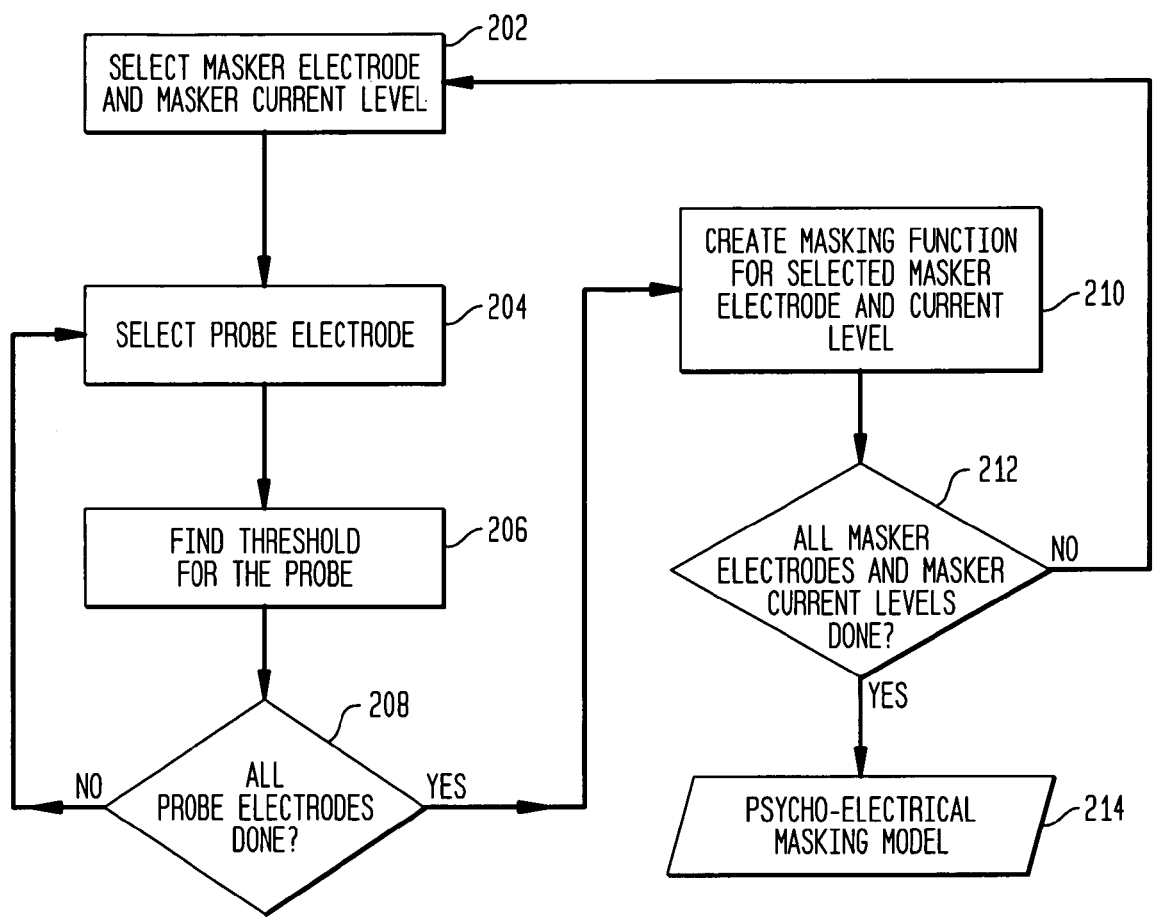
FIG. 2 illustrates a simplified flow chart of an exemplary method for generating a psychoelectric masking model, in accordance with one embodiment of the present invention.

FIG. 2 illustrates a simplified flow chart of a method for generating a psychoelectric masking model in accordance with one embodiment of the present invention. FIG. 2 will be described with reference to FIG. 1 where electrode array 134 includes a plurality of electrodes (for example, 22 electrodes). In the following description, two types of electrodes are referenced depending on the effect of their operation: masker electrodes and probe electrodes. A probe electrode is an electrode (or frequency in a tonal psychoelectric model) that is used to probe the amount of masking; the masker electrode is an electrode (or frequency in a tonal psychoelectric model) that potentially masks the probe electrode.

Initially at block 202, one of the electrodes of electrode array 134 is selected as the masker electrode and a current level is determined for stimulating the masker electrode. The current level for stimulating the masker electrode may be, for example, set as the Maximum Comfort Level (C-level) for the masker electrode, or some value below the C-level but greater than the Threshold current level (T-level) for the masker electrode. It should be appreciated that in alternative embodiments, the selected current level for the masker electrode may initially be below the T-level for the masker electrode.

Next, an electrode of electrode array 134 is selected as the probe electrode at block 204. The threshold for this probe electrode given the previously selected masker electrode and masker current level is determined at block 206. The threshold is the threshold current level for the probe electrode where stimulation for the probe electrode first becomes audible to the implant recipient in the presence of stimulation by the masker electrode at the masker current level. In psychoacoustics, this threshold is commonly referred to as a masked detection threshold.

In this example, the threshold may be determined by sequentially stimulating the masker electrode followed by the probe electrode. This technique is referred to herein as forward masking. In other embodiments, a backward masking technique may be used where the probe electrode is stimulated prior to the masker electrode. In other embodiments, the probe and masker electrodes are stimulated simultaneously, a technique referred to herein as simultaneous masking.

In determining the threshold, the probe current level (PCL) may initially be set at a low level and then be gradually increased until the implant recipient can hear the probe sound. The implant recipient may indicate whether or not they can hear any sound from the probe electrode by, for example, pressing down a button if they hear the sound and releasing it if the sound becomes inaudible. A further description of techniques for measurement of psychophysical forward masking is provided in Lawrence T. Cohen, Louise M. Richards, Elaine Saunders, and Robert S. C. Cowen, *Spatial Spread of Neural Excitation in Cochlear Implant Recipients: Comparison of Improved ECAP Method and Psychophysical Forward Masking,* 179 Hearing Res. 72-87 (May 2003) (hereinafter "the Cohen et al. 2003 paper"), which is hereby incorporated by reference herein.

After the threshold for this combination of masker and probe electrode is determined, it is next determined at block 208 whether other probe electrodes should be tested and their thresholds determined. Preferably the detection threshold for every combination of masker electrode and probe electrode is determined. Thus, if there are more probe electrodes for which to determine a threshold for this particular masker electrode, the process returns to block 204 and a next probe electrode is selected at block 204 and the operation performed at block 206 is performed for this combination of masker and probe electrodes.

After the thresholds for the probe electrodes of electrode array 134 are determined, a masking function for this masker electrode and masker current level is determined at block 210. A further description of exemplary techniques for determining masking functions is provided in the above-referenced Cohen et al. 2003 reference.

Next, at block 212 it is determined whether all masker electrodes and masker current levels have been selected. If not, the process returns to block 202 and the above operations are repeated for another masker electrode. If so, the psychoelectric masking model is determined at block 214 by combining the above-described masking functions. The measurements obtained in determining a psychoelectric model are hereinafter referred to as psychoelectric measurements.

The above psychoelectric measurements comprise a set of masking functions for different current levels for all electrodes available in electrode array 134. A masking function for a given electrode at a given current level is defined by masking thresholds (in current level or CL) for all electrodes in electrode array 134. As noted above, this psychoelectric model may be translated, if desired, to a tonal psychoelectric model so that instead of being in terms of CLs, it is in terms of sound pressure level (for example, dB) and visa versa. Additionally, rather than being in terms of electrodes, the measurements may also be translated so that they are in terms of the center frequencies of the frequency bands corresponding to the electrodes in array 134, and visa versa. The resulting masking model may then be used when taking masking effects into account when determining the stimulation signals to be used for stimulating electrode array 134, such as is described in further detail below.

Additionally, in another example, a psychoelectric model that is determined in terms of sound pressure levels (dB) (that is, a tonal psychoelectric model) can be translated into a psychoelectric model in terms of current levels. This may be accomplished by, for example, using a loudness growth function, such as, for example, a loudness growth function that is in terms of dB on one axis (the x-axis) and in terms of % CL on the other axis (Y-axis), where 100% CL represents the current level corresponding to the maximum point on the measurement curve. Additionally, this loudness growth function may, for example, be adapted for the implant recipient, and parameters, such as, for example, its steepness (Q-factor) may be adapted according to feedback from the implant recipient. As one of ordinary skill in the art would appreciate, it is not necessary to translate current level back to dB nor to translate electrode back to frequency, or visa versa. In alternative embodiments the values of either the psychoelectric model in terms of dB, current levels, or, for example, microvolts may be used when taking masking effects into account when selecting stimulation signals, as is described in further detail below.

As noted above, a cochlear implant uses a number of steps to calculate the stimulation current from the input sound level, such as, for example, filtering, selection, and loudness mapping (i.e., translating the acoustical energy into electrical current delivered to the electrodes). As one of ordinary skill in the art would appreciate; knowing the path that is used to translate acoustical to electrical parameters would allow for translation of the psychoacoustical model into the electric domain.

In addition to the above-noted method for determining psychoelectrical models, in other embodiments, other mechanisms may be used. For example, the above-described method of FIG. 2 may be adapted for determining a pscho-electrical model using electrophysiological measurements. In such an example, rather than determining a detection threshold using psychophysical measurements at block 206, the method determines the masking threshold based on electrophysiological measurements. These electrophysiological measurements may include, for example, measuring Electrical Compound Action Potentials (ECAP) of the auditory nerve, Electrically Evoked Auditory Brainstem Potentials (EABP) or Cortically Evoked Potentials (CEP). A more detailed description of exemplary methods for determining an electrophysiological model for use by a cochlear prosthesis is provided below.

In one embodiment, the cochlear prosthesis is a Nucleus® 24 cochlear implant system or a Nucleus® Freedom™ cochlear implant system, both of which are commercially available from Cochlear Limited, Australia. (NUCLEUS is a registered trademark and FREEDOM is a trademark of Cochlear Limited.) In such systems, electrode array 134 includes a plurality of electrodes (e.g., 22). Further, in this example, cochlear prosthesis 100 includes a version of Cochlear's Neural Response Telemetry (NRT™) software, such as, for example, Custom Sound EP™ software. (NRT and EP are trademarks of Cochlear Limited.) The NRT™ software and the Custom Sound EP™ software can be used to record ECAP potentials of the auditory nerve 138 in Nucleus™ 24 or Nucleus Freedom™ implant recipients. Further, a subtraction method may be used to minimize the stimulation artifact. For example, electrophysiological measurements measure nerve tissue potentials. The amplitudes of these potentials are typically in the 1-500 microvolt range and may be evoked by electrical stimuli that create an artifact that may by up to 10000 times larger than the response that is trying to be measured. Thus, a subtraction technique, such as discussed above may be used to minimize this artifact. A detailed description of an suitable subtraction method can be found in Abbas P J, Brown C J, Hughes M L, Ganz B J, Wolayer A A, Gervais J P and Hong S H, *Electrically evoked compound action potentials recorded from subjects who use the nucleus CI24M device*, Ann Otol Rhinol Laryngol Suppl. 2000 December; 185:6-9 (hereinafter "the Abbas et al 2000 paper"), which is hereby incorporated by reference herein.

A further description of masker and probe stimuli and their use in determining spread of excitation (SOE) curves for an implant recipient is provided in the above-referenced Cohen et al. 2003 paper and Lawrence T. Cohen, Elaine Saunders, and Louise M. Richardson, *Spatial Spread of Neural Excitation: Comparison of Compound Action Potential and Forward-Masking Data In Cochlear Implant Recipients*, 43 International Journal of Audiology 346-355 (2004), (hereinafter "the Cohen et al. 2004 paper"), which is hereby incorporated by reference herein.

Spread of excitation may, amongst other ways, be determined by varying the recording electrode. The recording electrode is the electrode used to take the electrophysiological measurements (e.g., ECAP) and may be any of the electrodes of electrode array 134. Additionally, the measured response typically decreases in amplitude as the recording electrode is moved away from the masker/probe electrode.

The subtraction method (described elsewhere herein with reference to the Abbas et al. 200 paper) and the "Masked Response Extraction technique" (also sometimes referred to as the "Miller technique") can also be used to create spread of excitation curves. The "Masked Response Extraction technique" (aka "Miller technique") is described in Miller C A, Abbas P J, Brown C J, *An Improved Method of Reducing Stimulus Artifact in the Electrically Evoked Whole Nerve Potential*, 21(4) Ear and Hearing 280-90 (August 2000), which is hereby incorporated by reference herein. A further description and comparison of mechanisms for generating SOE curves from ECAP measurements is provided in the above-referenced Cohen et al. 2003 paper and Cohen et al. 2004 paper.

Figure 3:
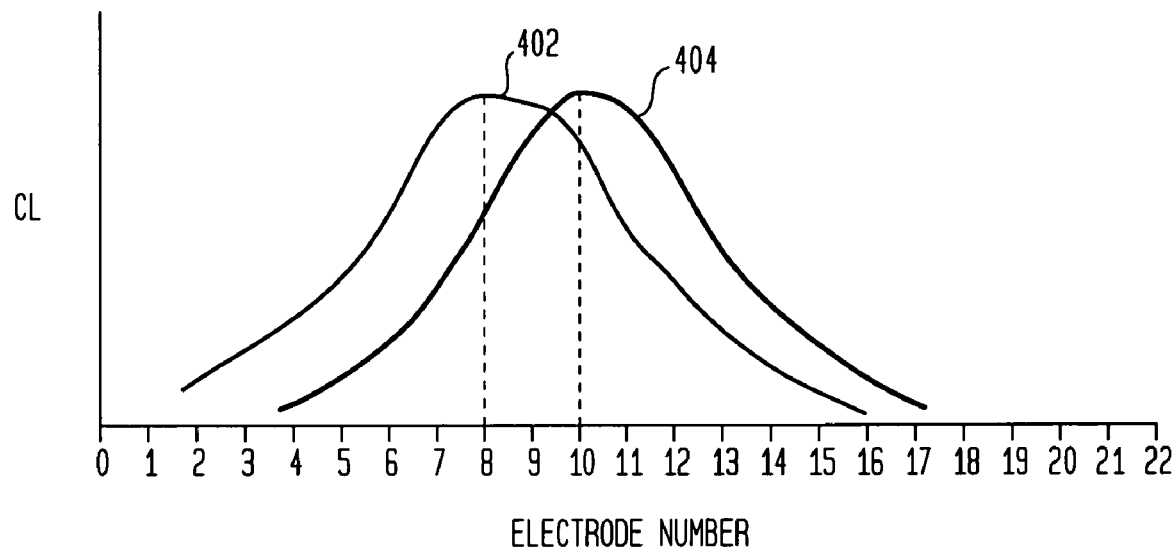
FIG. 3 illustrates a conceptual diagram of overlapping spread of excitations for a masker and a probe, in accordance with one embodiment of the present invention.

Additionally, in another embodiment, to determine the electrophysiological model, the masker and probe electrode need not be the same electrode, but instead may also be different electrodes. In such an example, cochlear prosthesis 100 may include Cochlear's NRT™ software. In this example, when the masker electrode is close to (or the same as) the probe electrode, the masking effect will be at a maximum, and as the masker and probe electrode get further apart the amount of the masking will decrease. For example, FIG. 3 illustrates a conceptual diagram of overlapping spread of excitations where the probe electrode is the $8^{th}$ electrode and the masker electrode is the $10^{th}$ electrode of electrode array 134. As illustrated, both the probe excitation field 402 and masker excitation field 404 overlap, thus indicating that there is substantial masking. This overlap may then be measured and used to generate an SOE curve.

Figure 4:
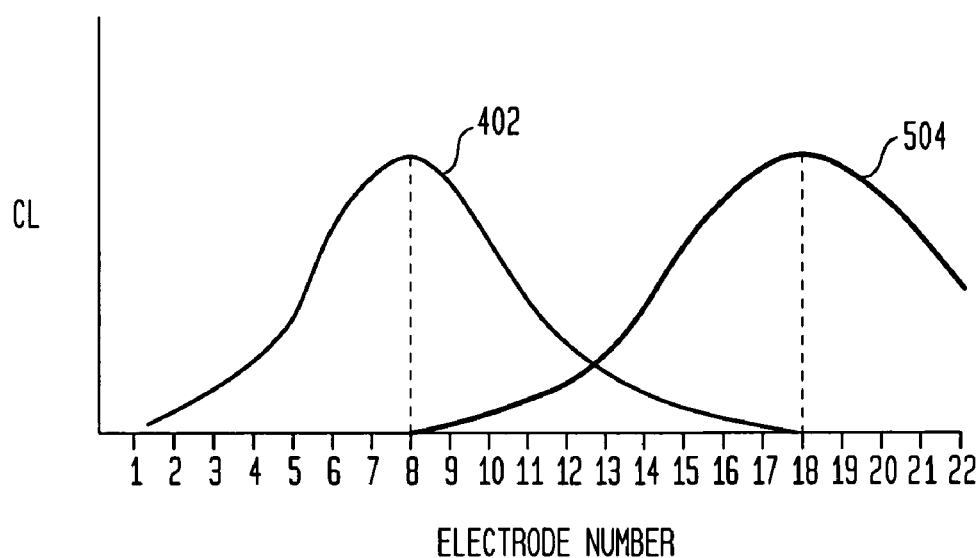
FIG. 4 illustrates a conceptual diagram of overlapping spread of excitations for a masker and a probe, in accordance with one embodiment of the present invention.

FIG. 4 illustrates a conceptual diagram of the overlapping spread of excitations where the probe electrode is still the $8^{th}$ electrode, but the masker electrode has been changed to the $18^{th}$ electrode. As illustrated, the masker's excitation field 504 and the probe's excitation field 402 slightly overlap. Together, FIGS. 3 and 4 illustrate that although there is still some masking where the masker electrode was the $18^{th}$ electrode (FIG. 4), it is less than the amount of masking where the masker electrode was the $10^{th}$ electrode (FIG. 3).

An SOE curve measured with the subtraction method for a particular probe electrode may be determined by, for example, taking measurements (e.g., ECAPs) for the probe electrode and every possible masker electrode (i.e., all 22 electrodes of electrode array 134). Then, an SOE curve for a different electrode may be determined by setting it as the probe electrode and taking measurements (e.g., ECAPS) of the amount of masking, again from all possible masker electrodes (e.g., all 22 electrodes). A further description of mechanisms for generating SOE functions where the masker and probe electrodes may be different is provided in the above-referenced Cohen et al. 2003 paper and Cohen et al. 2004 paper. Moreover, rather than taking measurements for every possible masker electrode, in other examples for determining an electrophysiological model, the masker electrode may be selected to be every other electrode, every fourth electrode, or may vary in any other appropriate way.

In generating the above-discussed SOE curves, various variables may be used, such as, for example, the probe rate, a masker-to-probe interval (MPI), the number of masking pulses, the rate of the masking pulses, an amplifier gain, the delay of the start of the measurement with respect to the probe pulse, the pulse widths, pulse gaps, or other variables applicable to the NRT™ software. For example, in one embodiment, the MPI interval may be set to +/−400 microseconds and all measurements taken at this MPI. However, in other embodiments, different MPIs may be used, or, for example, a set of measurements may be taken at one MPI value and then other sets of measurements taken at different MPI values. Further, lower MPI's may be used to mimic high stimulation rates. The number of masker pulses and the masker rate may be varied to mimic temporal effects at different stimulation rates. The probe rate is generally kept at a low rate (±50 Hz) to minimize adaptation effects. Likewise, the other variables may also remain fixed for all measurements, may vary, or different sets of measurements may be taken for different values. Additionally, summation effects of masker and probe pulses may be taken into account, such as, for example, when masker-to-pulse intervals are set to values below 300 microseconds.

Further, in the above examples discussing exemplary mechanisms for determining a psychoelectric model, the amplitudes of the stimuli for the masker electrode and the probe electrode may be set to be equal. This current level may be, for example, the Loudest Acceptable Perception Level (LAPL) for the probe electrode, or some value below the LAPL, such, as for example, 80% of the LAPL. Or in other examples, the amplitude for the masker electrode may be set to a value less than the Probe Current Level (PCL) (e.g., 80%, 60%, 40% of the PCL), or even a value greater than the PCL.

Further, in other examples, an SOE curve may be determined for one combination of PCL and masker current level, and then other SOE curves determined for different combinations of PCLs and masker current levels. Also, in other examples, information regarding the psychophysical threshold level and the LAPL for each electrode may be taken into account. For example, if the threshold level for a particular electrode that is being used as the masker electrode has a higher threshold level than other electrodes, a corresponding higher masker current level may be used when this particular electrode is the masker electrode.

Figure 5:
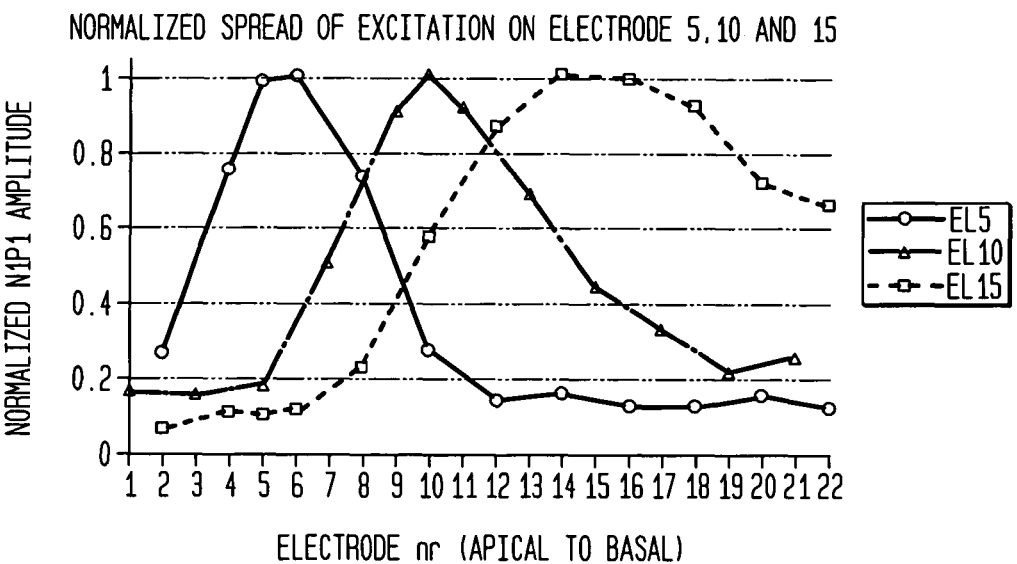
FIG. 5 illustrates exemplary spread of excitation (SOE) curves for an implant recipient where the Masker and Probe Current Levels were set to be equal, in accordance with one embodiment of the present invention.

FIG. 5 illustrates three exemplary spread of excitation (SOE) curves. In this example, a masker-to-probe interval (MPI) of 500 µs was used and the plotted psychoelectric measurements were normalized with respect to the maximum ECAP amplitude. The exemplary SOE curves illustrated in FIG. 5 depict normalized Spread of Excitation measurements carried out on 3 different electrodes (EL5, EL10 and EL15) in a Nucleus® Contour Advance™ recipient. As shown in FIG. 5, the overlap in excitation field may be deduced. For example, EL5 has an excitation field that has overlap with EL2 to EL10, EL10 has an excitation filed that has overlap with EL5 to EL16 and EL15 has overlap with EL8 to 22.

Figure 6:
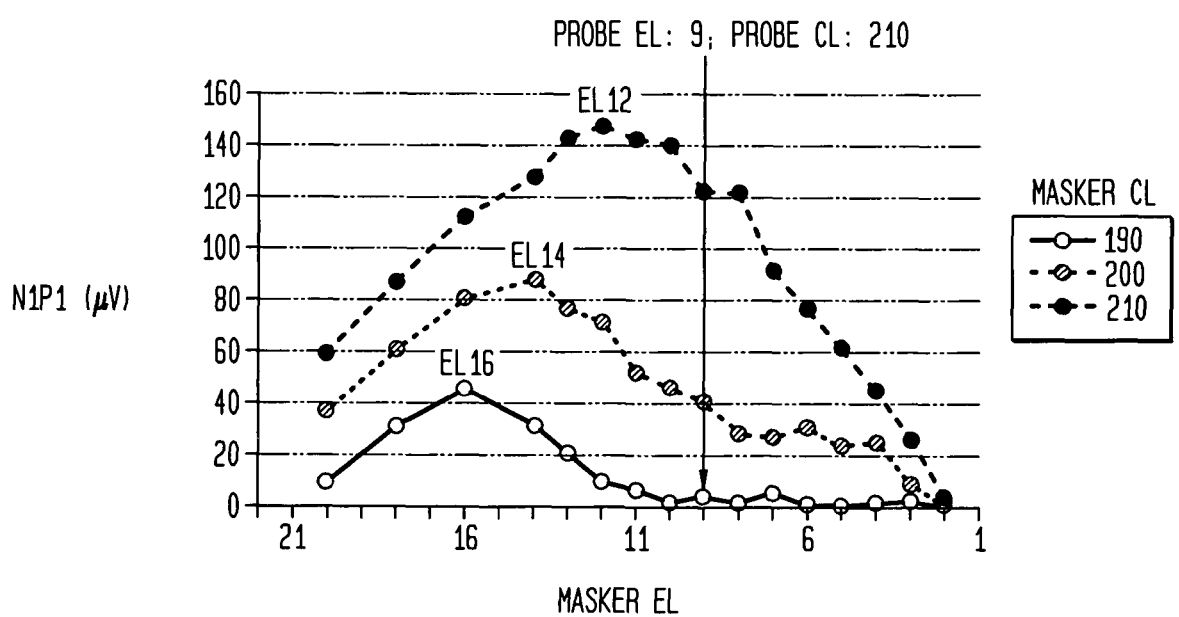
FIG. 6 illustrates another set of exemplary SOE curves for an implant recipient, in accordance with one embodiment of the present invention.

FIG. 6 illustrates another set of exemplary SOE curves for an implant recipient. In this example, the implant recipient was fitted with a CI24RE™ cochlear implant, the probe electrode was set as the $9^{th}$ electrode, and the probe current level was set at 210. Further, in this example, measurements were taken for three different masker current levels (190, 200 and 210). As illustrated, in this example, the SOE is not symmetrical around the probe electrode but is greater towards the apical end of the cochlea (i.e., electrode 12 for MCL=210, electrode 14 for MCL=200, and electrode 16 for MCL=190).

Moreover, if the determined SOE curves have a Y-axis that is in terms of microvolts, in an embodiment, this Y-axis is then translated to current levels (CL) for use when taking masking effects into account when determining the stimulation signals to be used, which is described in further detail below. One exemplary method for translating the Y-axis from microvolts to CL includes determining the dynamic range for each electrode; that is, the difference between the psychophysical threshold CL and the maximum comfort level CL for the electrode. Then, the masking thresholds in CL may be determined using the following simplified formula:

Masking Threshold on Electrode $X$=Threshold $CL$+ (($SOE$ Amplitude at Electrode $X$)/($SOE$ Maximum Amplitude))*(Dynamic Range of Electrode $X$)

As one of skill in the art would be aware, the above formula is a simplified formula for explanatory purposes, and that in actual implementations the formula would likely include additional variables.

Figure 7:
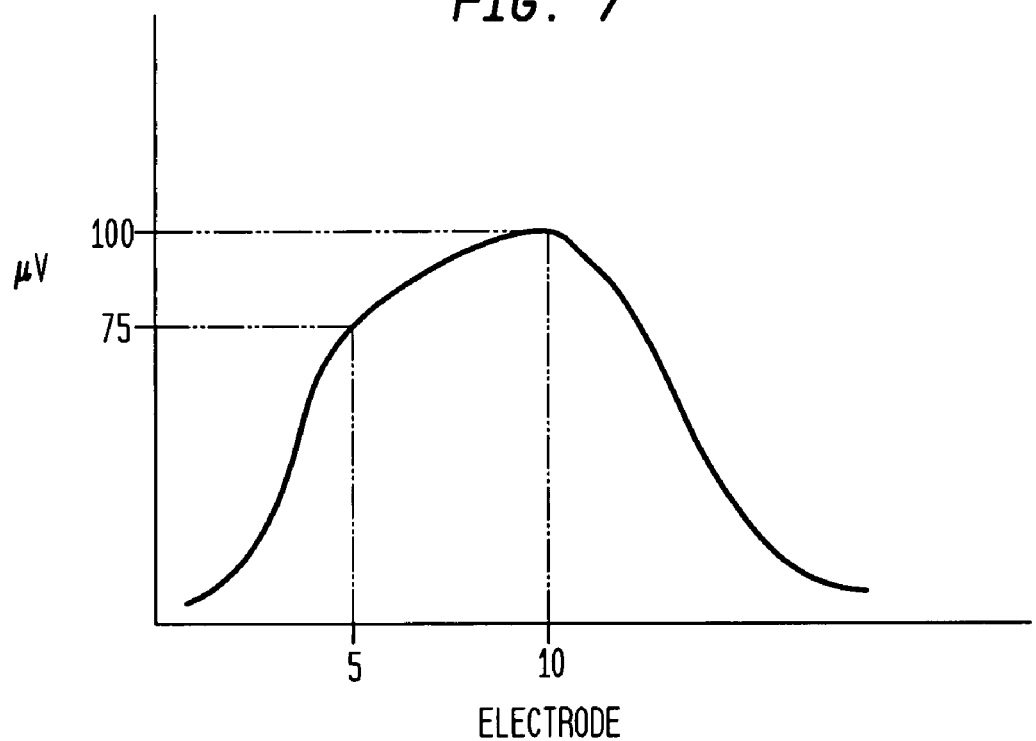
FIG. 7 illustrates an exemplary SOE curve, in accordance with one embodiment of the present invention.

FIG. 7 illustrates an exemplary SOE curve where the masker electrode is electrode 10 and the probe electrode is electrode 5. Further, in this example, electrode 5 has a threshold level of 170 CL and a maximum comfort level of 210 CL (not shown). Thus, the dynamic range for electrode 5 is 40 CL (210 CL–170 CL). As shown, the SOE curve has a maximum amplitude of 100 microvolts. Further, the amplitude of the SOE curve at electrode 5 is 75 microvolts. Thus, using the above calculation, the masking threshold for electrode 5 is equal to [170+((75)/(100)*40)] or 200 CL. This SOE curve may then be completely translated to CLs by, for example, repeating the above calculation for all electrodes on the X-axis (that is, all electrodes of electrode array 134). It should be noted that this is but one example of a method for translating an SOE curve from micro-volts to CLs, and other methods may be used without departing from the scope of the present invention.

For example, instead of using the psychophysical dynamic range of the electrode, one can use the amplitude growth function of the corresponding objective recording method that has been used for the recording of the SOE. The amplitude growth function then defines a transformation from CL to the amplitude of the objective recording in microvolts and vice versa. The threshold level of the response and the LAPL may be used to define the dynamic range and an offset level for a calculation like the one described above.

Further, in one example, once an SOE curve is determined and translated in terms of CLs, it may also be used to generate other SOE curves. Thus, rather than determining SOE curves for all possible combinations of probe electrode and current levels, some SOE curves may be interpolated or extrapolated from other SOE curves. For example, an SOE curve determined by measurements, such as those described above, may be used to generate other SOE curves, such as, for example, for different probe current levels. These interpolated SOE curves may be determined by multiplying all values in the original SOE curve by a particular factor. That is, if the maximum current level for the original SOE curve is 200 CL, it may be translated to an SOE curve with a maximum current level of 180 by multiplying all amplitudes by 9/10 (that is, 180/200). Or in another example, rather than multiplying all amplitudes by a factor, instead a value may be subtracted from all amplitudes. For example, an SOE curve with a maximum amplitude of 200 may be translated to an SOE curve with a maximum amplitude of 180 by subtracting 20 from all the amplitudes.

In addition, to shift SOE curves on the Y-axis (i.e., by amplitudes), these translated curves may also be shifted in the X-axis; that is, shift by electrodes. As with Y-axis shifting, this may also be accomplished by multiplying a factor to the X-axis points (that is, electrodes) or subtracting values from the X-axis points.

Figure 8:
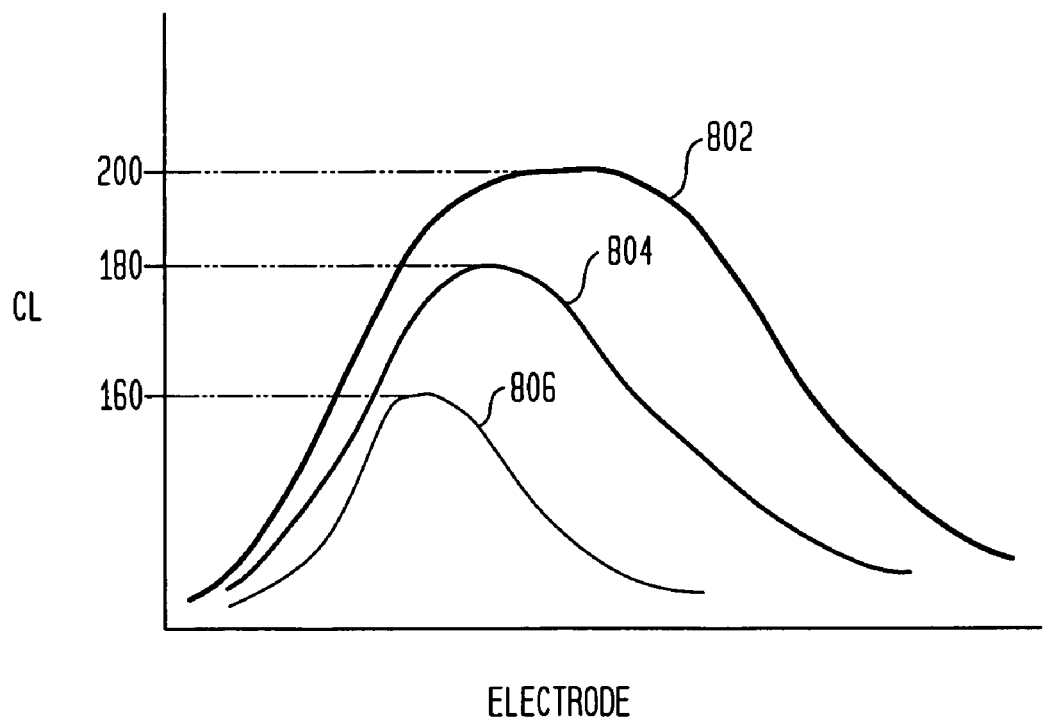
FIG. 8 illustrates a set of exemplary SOE curves exhibiting both Y-axis and X-axis shifting, in accordance with one embodiment of the present invention.

FIG. 8 illustrates a set of exemplary SOE curves exhibiting both Y-axis and X-axis shifting. As illustrated, SOE curve 802 has a maximum current level of 200. This curve may have been determined using a method such as those discussed above. SOE curve 804 may then be generated by translating SOE curve 802 from a maximum current level of 200 to a maximum current level of 180. This may be accomplished by, for example, multiplying the amplitudes of SOE curve 802 by a factor (i.e., 9/10) or by subtracting all amplitudes by a value (i.e., 20). Additionally, the X-axis is also being illustrated as shifting from left to right. This may be accomplished by multiplying or subtracting a value from the X-axis. This value may be based on laboratory measurements indicating an appropriate value for X-axis shifting for this particular implant recipient, or a population of people to which this implant recipient belongs, or the population as a whole. FIG. 8 further illustrates an SOE curve 806 with a maximum current level of 160 that is also generated from translating SOE curve 802 in a like manner. These collections of SOE curves may then be used as the electrophysiological model used for taking masking into account when determining the stimulation signals for stimulating electrode array 134. That is, these SOE curves may be combined with any other SOE curves determined for other electrodes, as described above with reference to block 214 of FIG. 2.

FIG. 6 in the Cohen et al. 2003 paper shows that psychoelectric measured forward masking curves and electro-physiologically measured SOE curves have a clear correlation. This suggests that the use of both masking models would give similar results when used in a compression algorithm. The advantage of the electrophysiological model is that it can be obtained without subjective feedback from the cochlear implant recipient. This is particularly important in young children or psychologically disabled cochlear implant recipients for whom detection of psychophysical masking would not be practicably feasible.

Although the above embodiments for determining an electrophysiological model for a particular implant recipient were discussed with reference to ECAP measurements, in other examples other electrophysiological measurements may be used, such as, for example, electrical auditory brainstem responses (EABRs) or cortically evoked potentials (CEPs).

Figure 9:
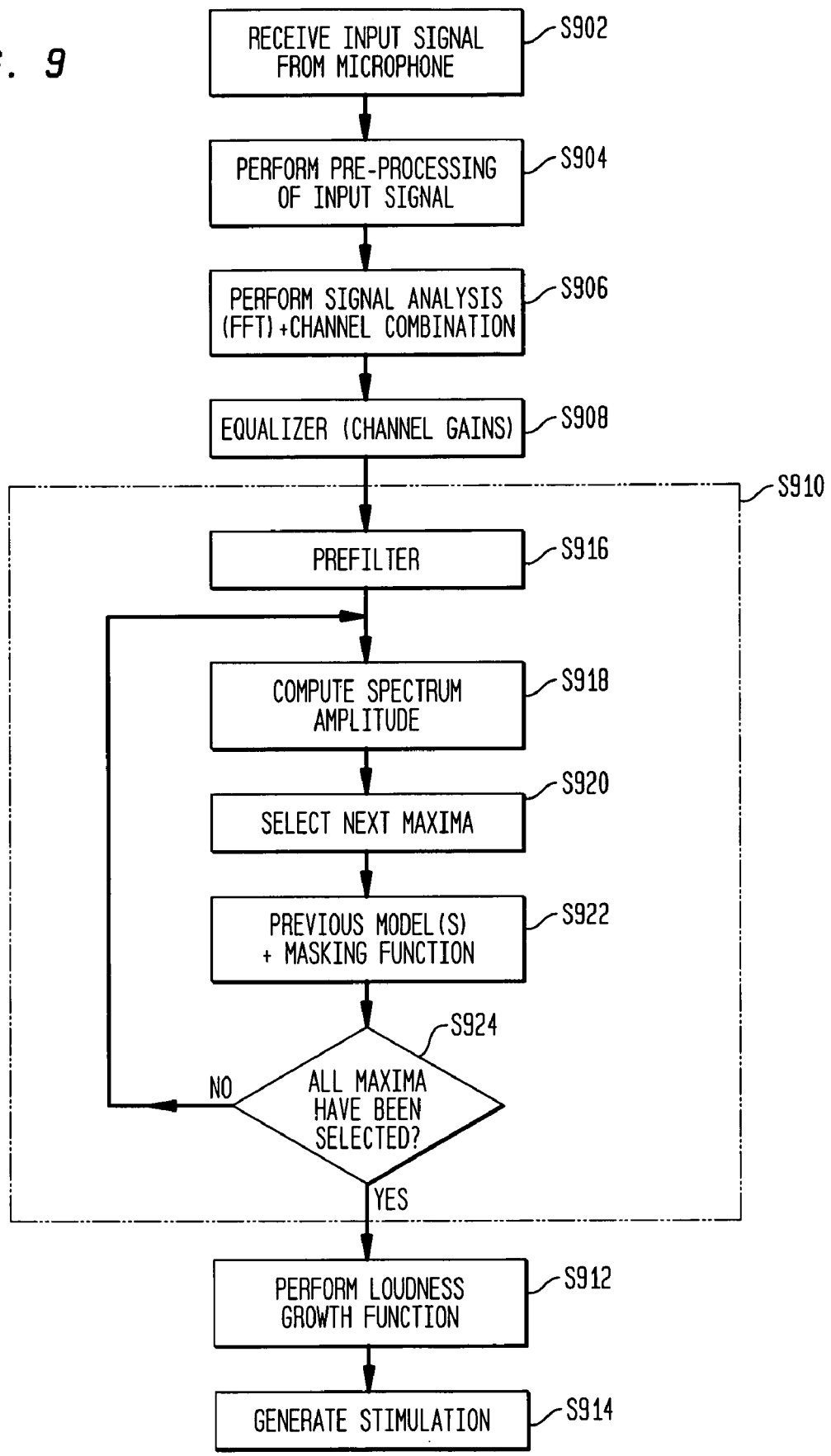
FIG. 9 illustrates an exemplary method for receiving and masking signals, in accordance with one embodiment of the present invention.

FIG. 9 illustrates an exemplary method for receiving and masking signals, in accordance with embodiments of the present invention. At block 902, microphone 120 receives sounds which are converted to electrical signals. These signals may then undergo pre-processing at block 904. This pre-processing may, for example, include using a pre-emphasis filter, automatic gain control (AGC), and/or manual sensitivity control (MSC), such as for example used in the Advanced Combination Encoder (ACE) strategy.

These signals next undergo signal analysis at block 906. This may include filtering the signals using a bank of bandpass filters to obtain a plurality of signals as is well-known to those of ordinary skill in the art. Moreover, in a cochlear prosthesis 100 where electrode array 134 includes 22 electrodes, the signal analysis preferably outputs 22 separate output signals, one corresponding to each electrode of electrode array 134. Additionally, in an alternative embodiment, virtual channels may also be generated by, for example, combining the stimulation signals for multiple electrodes, thus resulting in possibly more than 22 output signals. For example, a virtual channel may be for a frequency between the frequencies corresponding to two electrodes of electrode array 134. Then, by appropriately stimulating two or more of the electrodes of electrode array 134, the frequency corresponding to the virtual channel may be perceived by the recipient. For example, intermediate frequencies corresponding to a virtual channel may be achieved by coordinated stimulation of, for example, three electrodes that together cover a frequency band including the desired intermediate frequency. For example, the three electrodes (referred to herein as a triad) may be stimulated at particular amplitudes and according to a particular timing pattern so that the intermediate frequency is perceived by the implant recipient. Or for example, a virtual channel may be used to cause multiple electrodes to be simultaneously stimulated, thus resulting in application of a stimulus to the auditory nerve 138 having a larger spread of excitation (SOE).

These virtual channels may be treated identically to real channels in the presently described embodiments. That is, although the present embodiments are described with reference to a one to one correspondence between electrodes and stimulation channels, in other embodiments, virtual channels may be used and treated in the same manner, for masking purposes, as real channels. For example, rather than simply determining the psychoelectric model in terms of electrodes (i.e., real channels), such as described above with reference to FIGS. 2-8, a psychoelectric model in terms of stimulation channels (i.e., both real and virtual channels) may be determined. In such an example, similar methods to those discussed above may be used for determining the psychoelectric model.

Figure 10:
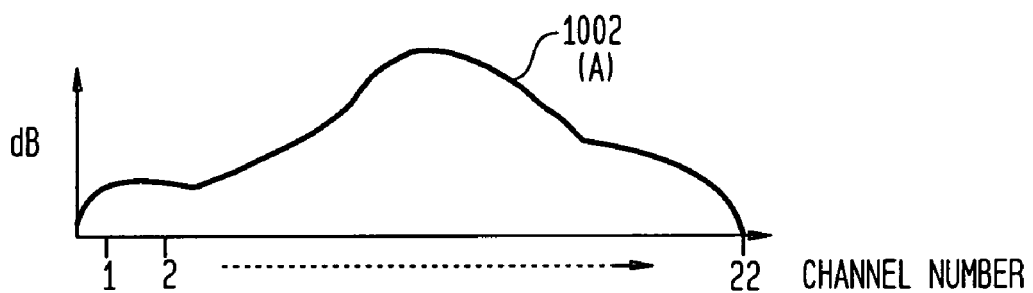
FIG. 10 illustrates an exemplary frequency spectrum of an exemplary received signal, in accordance with one embodiment of the present invention.

Further, rather than using a plurality of bandpass filters, a Fast Fourier Transform (FFT) may be used to generate the frequency spectrum for the received signal. In such an example, the FFT may, for example, compute 22 spectrum amplitudes (one for each electrode) between 125 and 8 kHz. Further, as discussed above, virtual channels may be employed allowing for the number of channels to be greater than the number of electrodes. After signal analysis, the resulting signals may then be equalized at block 908. FIG. 10 illustrates an exemplary frequency spectrum 1002 of an exemplary received signal after equalization.

The signal is then compressed and stimulation signals are selected for use by electrode array 134 at block 910. A further description of exemplary methods for compressing the signal are presented below. Next, a loudness growth function may be used on the selected stimulation signals at block 912. After which, the signals may be sent to electrode array 134 for stimulating auditory nerve 138 at block 914. As discussed above, these stimulation signals may be real channels (i.e., corresponding to a single electrode) and/or virtual channels involving, for example, the simultaneous or coordinated stimulation of multiple electrodes.

The following provides a more detailed description of one exemplary method for compressing the signal at block 910. This exemplary method may, for example, be performed by the speech processing unit 116 of cochlear prosthesis 100. Or in other examples, the following method may be performed by other hardware or software, or any combination thereof. Moreover, the following provides one exemplary method, and other methods may be used without departing from the invention.

Figure 11:
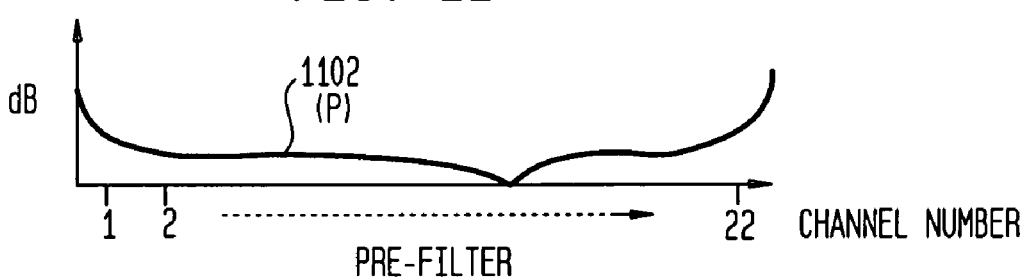
FIG. 11 illustrates an exemplary frequency spectrum of a pre-filter for pre-processing of the signal, in accordance with one embodiment of the present invention.

First, a frequency spectrum for pre-filtering the signal is determined at block 916. FIG. 11 illustrates an exemplary frequency spectrum 1102 of a pre-filter that may be used for pre-processing of the signal. In this example, the exemplary frequency spectrum for the pre-filter. As illustrated, this exemplary pre-filter approximates an equal loudness function. A further explanation of such an exemplary pre-filter is provided in the above-referenced Baumgarte reference. For example, the pre-filter may be used to compensate for varying thresholds-in-quiet at different frequencies (e.g., the electrodes corresponding to the frequencies). That is, as is well known to those of ordinary skill in the art, a threshold in quiet is used to compensate for the fact that a normal hearing person does not hear every frequency with the same intensity. The pre-filter may then, for example, be an equal loudness function that compensates for these varying thresholds in quiet.

Figure 12:
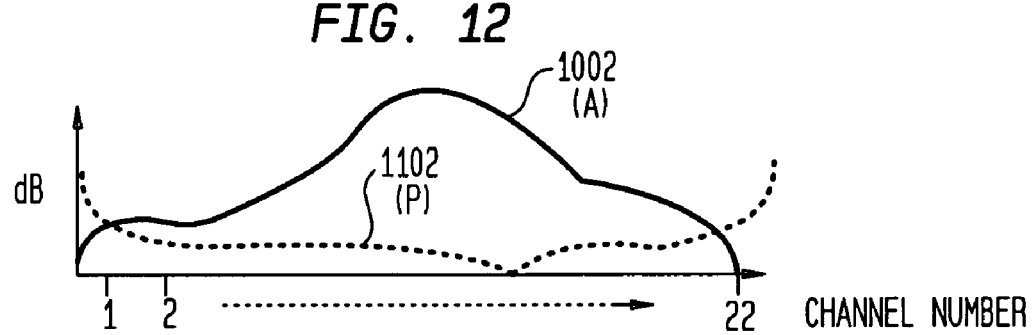
FIG. 12 further illustrates the combination of the frequency spectrum of the exemplary received signal and the frequency spectrum of a pre-filter, in accordance with one embodiment of the present invention.
Figure 13:
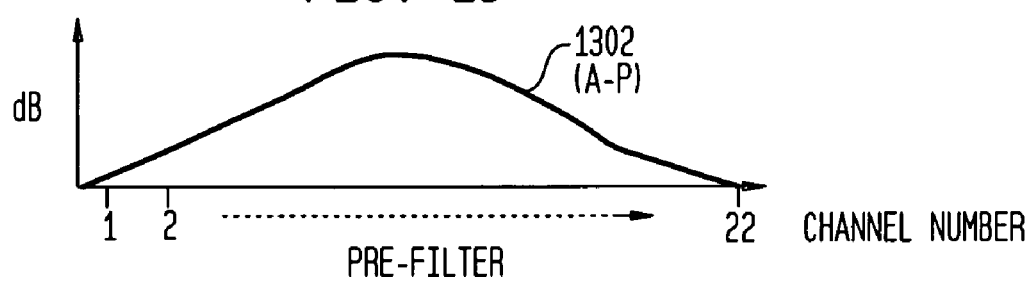
FIG. 13 illustrates a total masking effect resulting from the frequency spectrum illustrated in FIG. 12.
Figure 14:
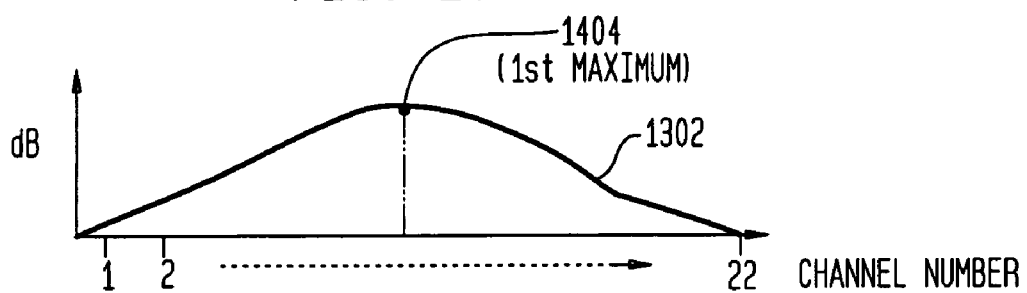
FIG. 14 illustrates a frequency spectrum along with a determined maxima, in accordance with one embodiment of the present invention.

Next, the computed frequency spectrum is applied to the received signal block 918. FIG. 12 further illustrates the combination of the frequency spectrum 1002 (FIG. 10) of the exemplary received signal and the frequency spectrum 1102 (FIG. 11) of the pre-filter and FIG. 13 illustrates the resulting frequency spectrum 1302 (i.e. frequency spectrum 1002 minus frequency spectrum 1102). After application of the computed spectrum to the received signal, the maxima (that is, the channel having the largest amplitude) for the resulting spectrum is determined at block 920. FIG. 14 illustrates resulting frequency spectrum 1302 along with the determined maxima 1404.

After the maxima is determined, the masking effect that would be caused by the selected maxima is determined and this masking effect is combined with the frequency spectrum 1102 of the pre-filter at block 922. The masking effect of the selected maxima is preferably determined using one of the above-discussed models. For example, a psychoelectric model determined for this user may be used. Moreover, rather than using a psychoelectric model generated for this particular implant recipient, in other examples, a psychoelectric model for a particular group of people may be used. For example, if for some reason it is not possible or desirable to measure the masking effect for the implant recipient, the system may instead use a psychoelectric model for a group of people (e.g., implant recipients) sharing a common characteristic with the implant recipient (e.g., age, gender, etc.). Or, for example, the system may use a psychoacoustic model, such as, for example, a generic psychoacoustic model for the population as a whole, such as, for example, the MPEG1 Psychoacoustic Model 1 or Model 2. Or, the system may use a psychoacoustic model for a particular group of people (e.g., people with normal hearing) sharing a common characteristic with the implant recipient (e.g., age, gender, etc.). Additionally, the masking model utilized may be in terms of dB, CL, or microvolts, and as discussed above these models may be translated into one another. In this example, the selected model is translated into a model in terms of CLs and electrodes (if necessary), and this model is used in determining the masking effects for the selected maxima. The combination of the masking effect and the pre-filter will be referred to as the total masking effect.

Figure 15:
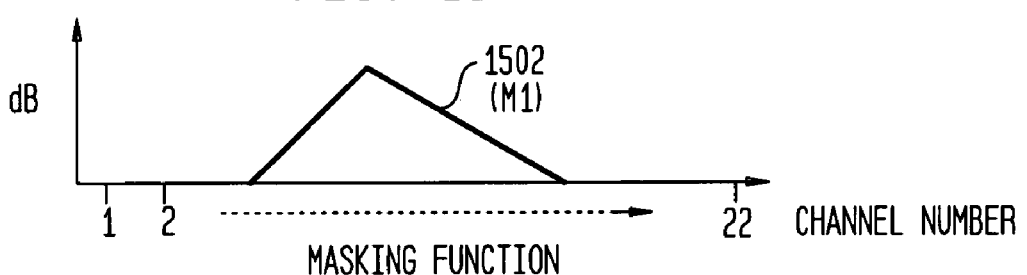
FIG. 15 illustrates an exemplary frequency spectrum of the masking effect for a selected maxima, in accordance with one embodiment of the present invention.
Figure 16:
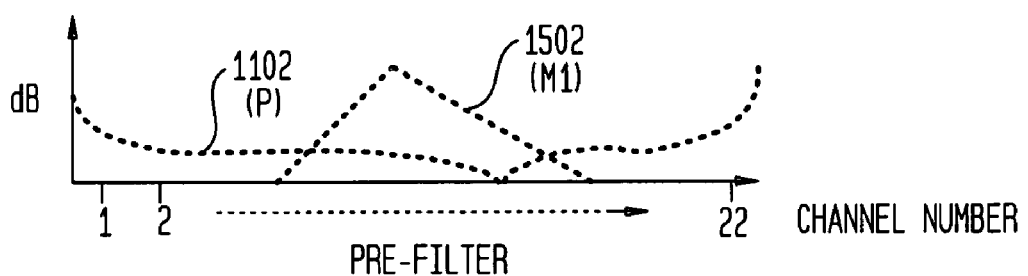
FIG. 16 illustrates an exemplary frequency spectrum of the masking effect for a selected maxima along with the frequency spectrum of a pre-filter, in accordance with one embodiment of the present invention.
Figure 17:
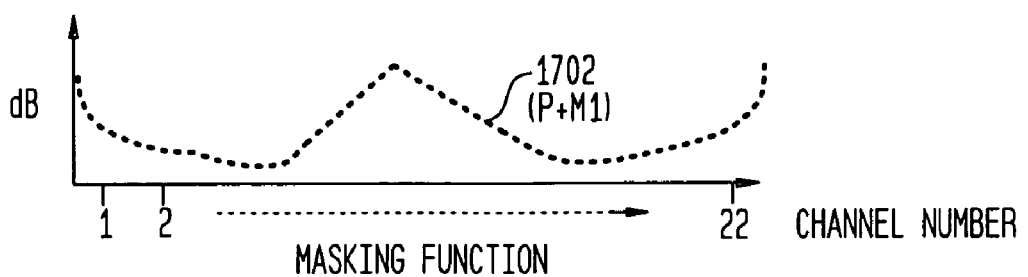
FIG. 17 illustrates a resulting total masking effect, in accordance with one embodiment of the present invention.

FIG. 15 illustrates the exemplary frequency spectrum 1502 of the masking effect for the selected maxima 1404. That is, FIG. 15 is a curve that indicates for each frequency the amount of masking as attenuation in dB. FIG. 16 illustrates the exemplary frequency spectrum 1502 of the masking effect for the selected maxima 1404 along with the frequency spectrum 1102 of the pre-filter. FIG. 17 illustrates the resulting total masking effect 1702 (that is, frequency spectrum 1502 plus frequency spectrum 1102). Although additive here, the total masking effect 1702 may be non-linear or something other that the sum.

Next, it is determined whether all desired maxima have been determined at block 924. For example, in one embodiment it may be desirable to determine 8 maxima for stimulation of electrode array 134. Thus, in this example, the process will continue until all 8 maxima are determined or until the total masking effect indicated that no other maxima needs to be determined (for example, the difference between the frequency spectrum of the received signal and the combined frequency spectrum of the masking effects is equal or smaller than a predefined threshold.). In an alternative embodiment, a dynamic number of maxima are determined based on the amount of information in the signal. For example, if there is a large broad peak, there is a single maxima, while if there are multiple narrower peaks more maxima will be stimulated. In other words, in this embodiment, the number of maxima dynamically depends on the spectral shapes and amount of masking. It should be appreciated that it is possible to adjust the stimulus artifact to make a loudness correction based on a loudness model.

Figure 18:
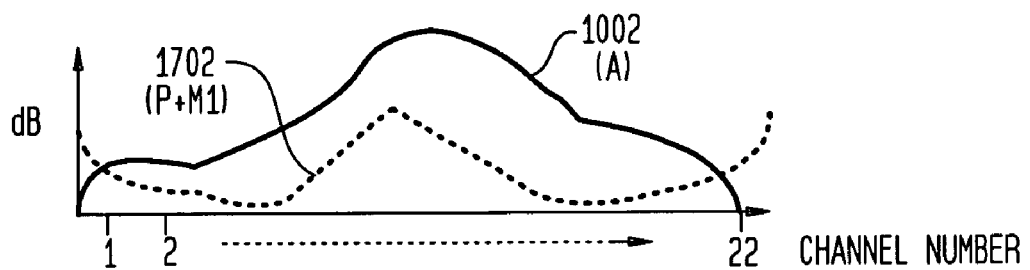
FIG. 18 illustrates the exemplary frequency spectrum of a total masking effect and the frequency spectrum of a received signal, in accordance with one embodiment of the present invention.
Figure 19:
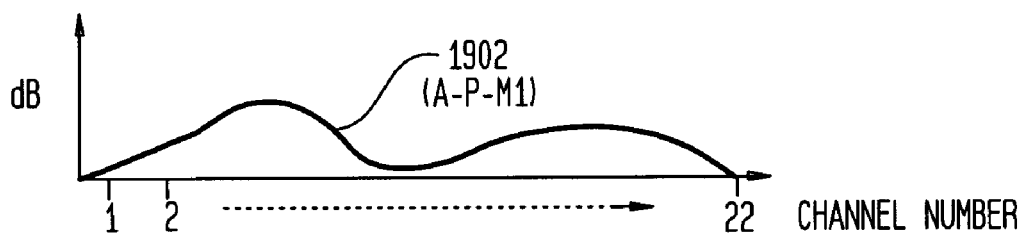
FIG. 19 illustrates a resulting frequency spectrum, in accordance with one embodiment of the present invention.
Figure 20:
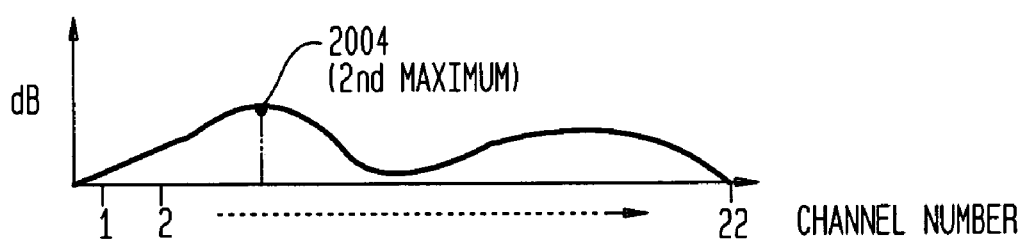
FIG. 20 illustrates a frequency spectrum along with a determined maxima, in accordance with one embodiment of the present invention.

If more maxima should be determined, the process returns to block 918 and the total masking effect is applied to the received signal (in this particular example it is subtracted) at block 922. FIG. 18 illustrates both the exemplary frequency spectrum 1702 of the total masking effect and the frequency spectrum 1002 of the received signal. FIG. 19 illustrates the resulting frequency spectrum 1902 (i.e. frequency spectrum 1002 minus frequency spectrum 1702). The next maxima is then determined at block 920. FIG. 20 illustrates frequency spectrum 1902 along with determined maxima 2004. Next, the masking effect of this next maxima is determined and is combined with the masking effects of the prior selected maxima and the prefilter at block 922.

If more maxima should be determined at block 924, the process again returns to block 918 and the combined total masking effect is then subtracted from the frequency spectrum 1002 of the received signal and another maxima determined. This process may then repeat until all desired maxima are determined.

Figure 21:
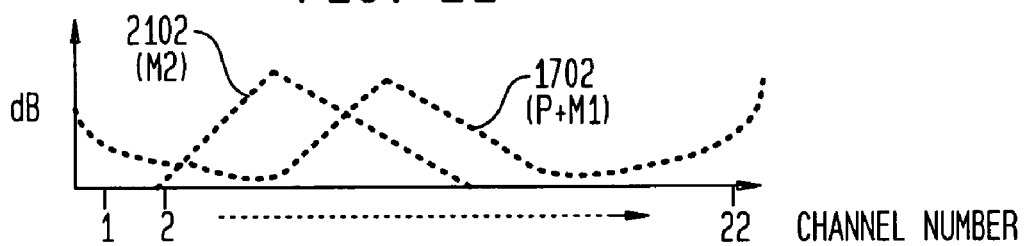
FIG. 21 illustrates a frequency spectrum of a new masker along with a prior determined total masking effect, in accordance with one embodiment of the present invention.
Figure 22:
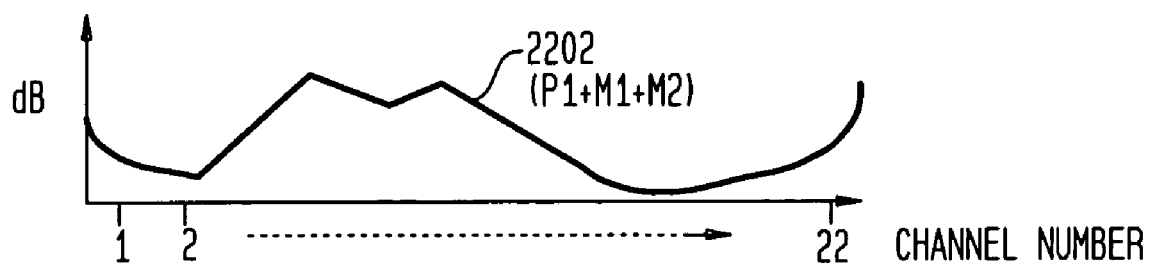
FIG. 22 illustrates a total masking effect frequency spectrum, in accordance with one embodiment of the present invention.
Figure 23:
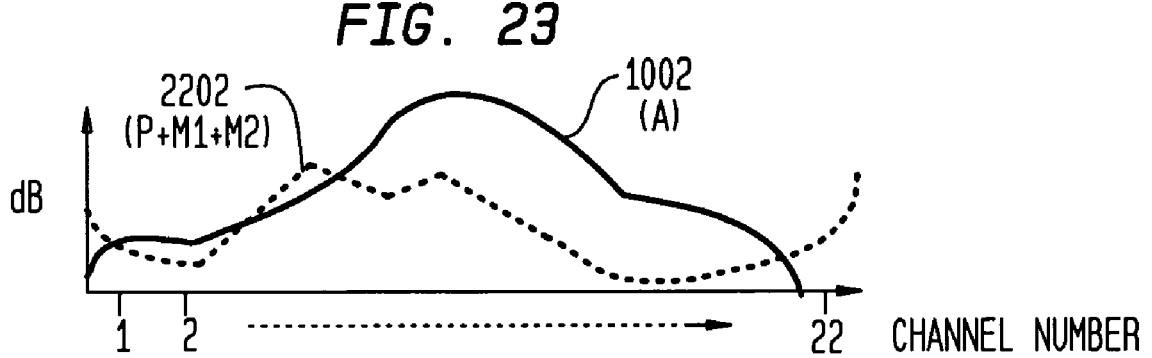
FIG. 23 illustrates a total masking effect frequency spectrum 2102 and a frequency spectrum of a received signal, in accordance with one embodiment of the present invention.
Figure 24:
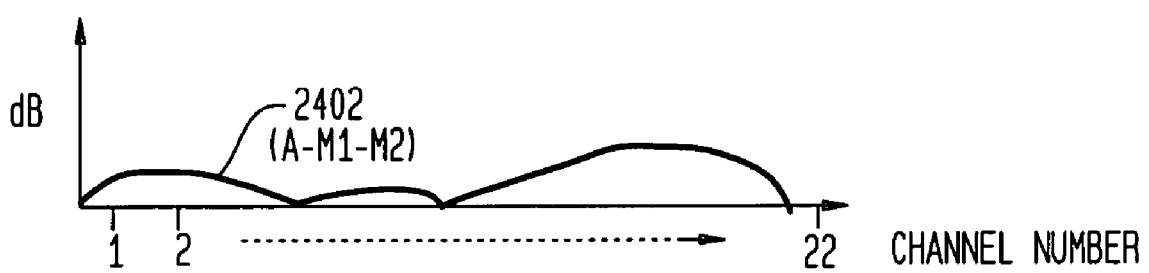
FIG. 24 illustrates a resulting frequency spectrum, in accordance with one embodiment of the present invention.

For example, FIG. 21 illustrates the frequency spectrum 2102 of this new masker along with the prior determined total masking effect 1702. These combine to create the total masking effect frequency spectrum 2202 illustrated in FIG. 22. This total masking effect spectrum 2202 is then subtracted from the frequency spectrum of the received signal 1002 as illustrated in FIG. 23. This results in frequency spectrum 2402 illustrated in FIG. 24. The maxima for this resulting spectrum may then be determined and the process repeated, for example, until all maxima are determined or no other maxima can be determined.

The above described method illustrated in FIG. 9 provides one example of a method for taking masking effects into account when determining stimulation signals for use in an cochlear prosthesis 100. Other methods of course can be used without departing from the invention. Moreover, as would be apparent to one of skill in the art, the above described steps may be interchanged, combined, or replaced with other steps without departing from the invention, which is defined in the below claims.

For example, in an embodiment block 910 may involve application of a simple psychoelectric model, such as for example, an N+X scheme, were X=1, 2, etc. In such an example, the stimulation signal having the largest amplitude is selected. Then the channels (e.g., electrodes) within X channels (e.g., electrodes) of the selected channel on both sides of the selected channel are deemed masked and therefore not eligible for selection. Then, the next highest signal is selected and the channels (e.g., electrodes) within X channels (e.g., electrodes) of this selected signal are deemed masked and not eligible for selection. This process then may be repeated until all maxima are selected.

In another embodiment, after the measurements for the implant recipients are taken, they are used to create a masking table for the implant recipient. Or, in other examples, a generic masking table may be used that applies, for example, to the population as a whole or to a particular subset of the population to which the implant recipient shares a common characteristic. Additionally, this masking table may be based on psychophysical measurements including psychoelectric or electrophysiological measurements.

The masking table may, for example, include a set of minimum masked threshold level for each electrode of electrode array 134. For each electrode there is a list of masking levels for the other electrodes, that if the particular electrode is stimulated, the other electrodes will not be stimulated unless their amplitude is above their masking level. For each electrode these unmasking levels can be specified in absolute CLs or relative percentages to the stimulation of the original electrode. An exemplary masking table is listed below for one electrode, n.

As shown, the masking table may include a column identifying each electrode of electrode array 134 along with corresponding minimum unmasked levels. Each unmasked level may, for example, give the minimum stimulus level (e.g., minimum current level) to electrode n which will elicit a response immediately following a stimulus to one or more relevant electrodes. In a complete masking model all electrodes of the array could be considered as relevant. Further, these minimum levels may be expressed as values between the psychophysical threshold (T) and psychophysical maximum comfort (C) levels of the corresponding electrode. The threshold (T) and maximum comfort (C) levels may be determined during the fitting of cochlear prosthesis 100.

| MINIMUM UNMASKED LEVELS | |
|---|---|
| Electrode | Minimum Unmasked Levels |
| 1 | $M_{1,T}, M_{1,T+1}, \ldots M_{1,C-1}, M_{1,C}$ |
| 2 | $M_{2,T}, M_{2,T+1}, \ldots M_{2,C-1}, M_{2,C}$ |
| ... | ... |
| n − 1 | $M_{n-1,T}, M_{n-1,T+1}, \ldots M_{n-1,C-1}, M_{n-1,C}$ |
| n + 1 | $M_{n+1,T}, M_{n+1,T+1}, \ldots M_{n+1,C-1}, M_{n+1,C}$ |
| ... | ... |
| ... | ... |

It should be understood this is but one example of a masking table and other types of masking tables may be used without departing from the invention. This determined table may then be used in implementing a masking scheme to delete or replace signals.

Figure 25:
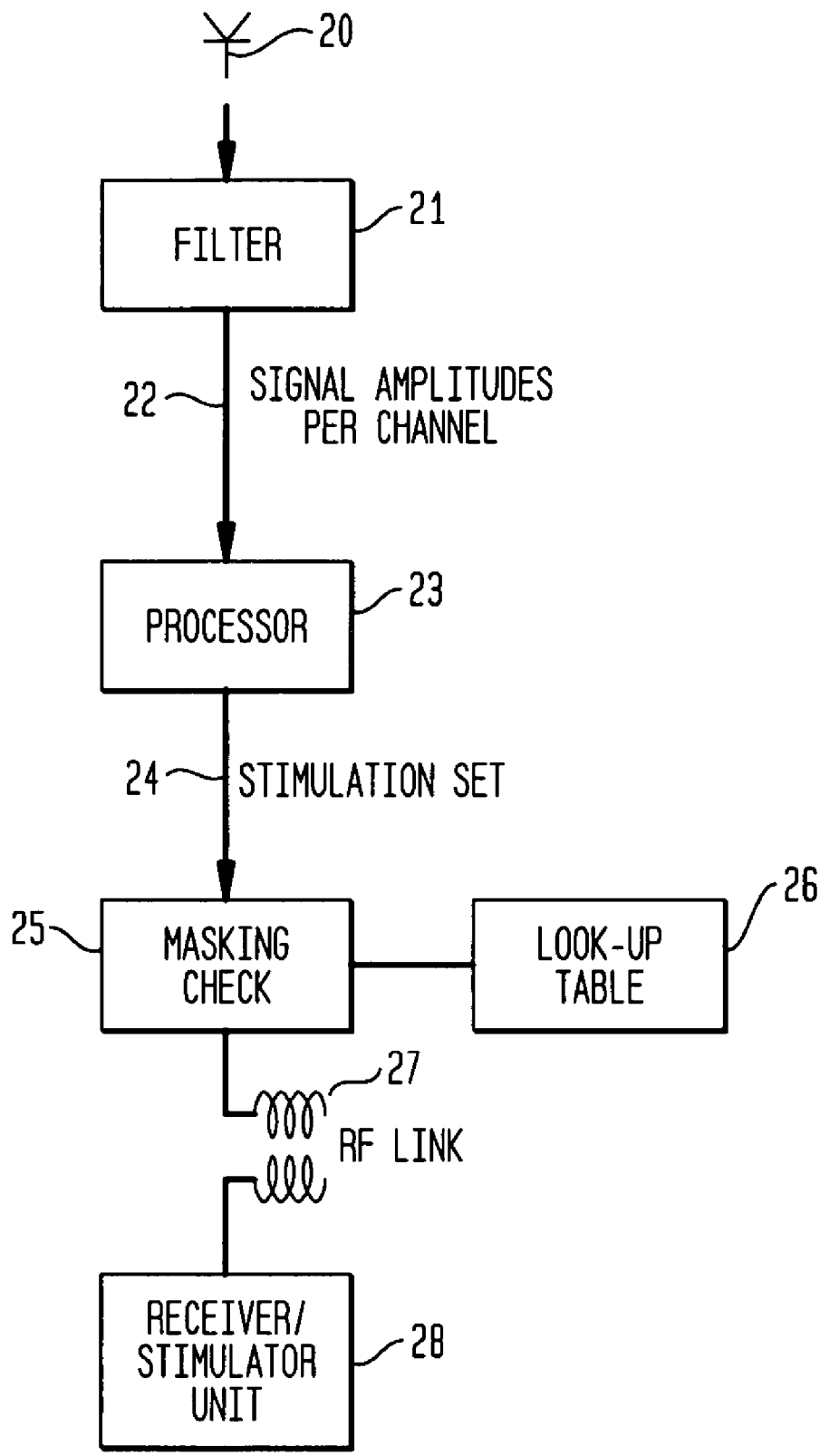
FIG. 25 illustrates an exemplary flow chart of a method for checking of masked signals, in accordance with one embodiment of the present invention.

FIG. 25 illustrates an exemplary flow chart of a method for masking signals. As illustrated, sound signals are detected by microphone 20. These signals are then processed into a predetermined number of frequency channels by filter 21. The output of filter 21 is a set of signal amplitudes per channel 22. Processor 23, in simple terms, selects certain channels as the basis for stimulation, based on amplitude or other factors. A set of stimulation instructions for implanted receiver stimulator unit 28 is thereby produced. These instructions include at least the electrode or electrodes to be stimulated, and the amplitude of the stimulus to be applied. These steps may also include, for example, the processing and equalization discussed above with reference to FIG. 9. Moreover, these steps may occur in speech processing unit 116 or, for example, in other hardware or software or any combination thereof.

After the stimulation signals are generated and processed, they may next undergo a Masking Check 25. Masking Check 25 involves comparing each successive two or more stimuli with the look-up table to determine whether they match a predetermined masking rule in look-up table 26. Further, the masking table 26 and masking check 25 may be stored and performed by speech processing unit 116, or by, for example, other hardware or software, or any combination thereof.

The masking check output is thus the stimulation set, with masked stimuli excluded. This is then transmitted conventionally, for example via an RF link 27 to the implanted receiver/stimulator unit 28, which operates conventionally.

In an embodiment, both a psychoacoustic model and a psychoelectric model may be used for masking signals. For example, a psychoacoustic model may be applied first to exclude stimulation pulses that are redundant to a normal hearing person because they are masked. Then, a psychoelectric model (e.g., a user specific model) may be used to remove stimulation pulses that are redundant to the implant user because they will be masked (i.e., the signal would be masked by another larger amplitude signal). This scheme would lead to a power saving (less stimulation) without loss of performance. Or, alternatively, a psychoelectric model may be used to determine what signals would be masked, and then boost their amplitude to compensate for the electrical masking that is not present in normal hearing This may lead to improved perception of the sound. This permits signals that would be heard by a normal hearing person, but masked for an implant recipient, to be perceived by the implant recipient.

Figure 26:
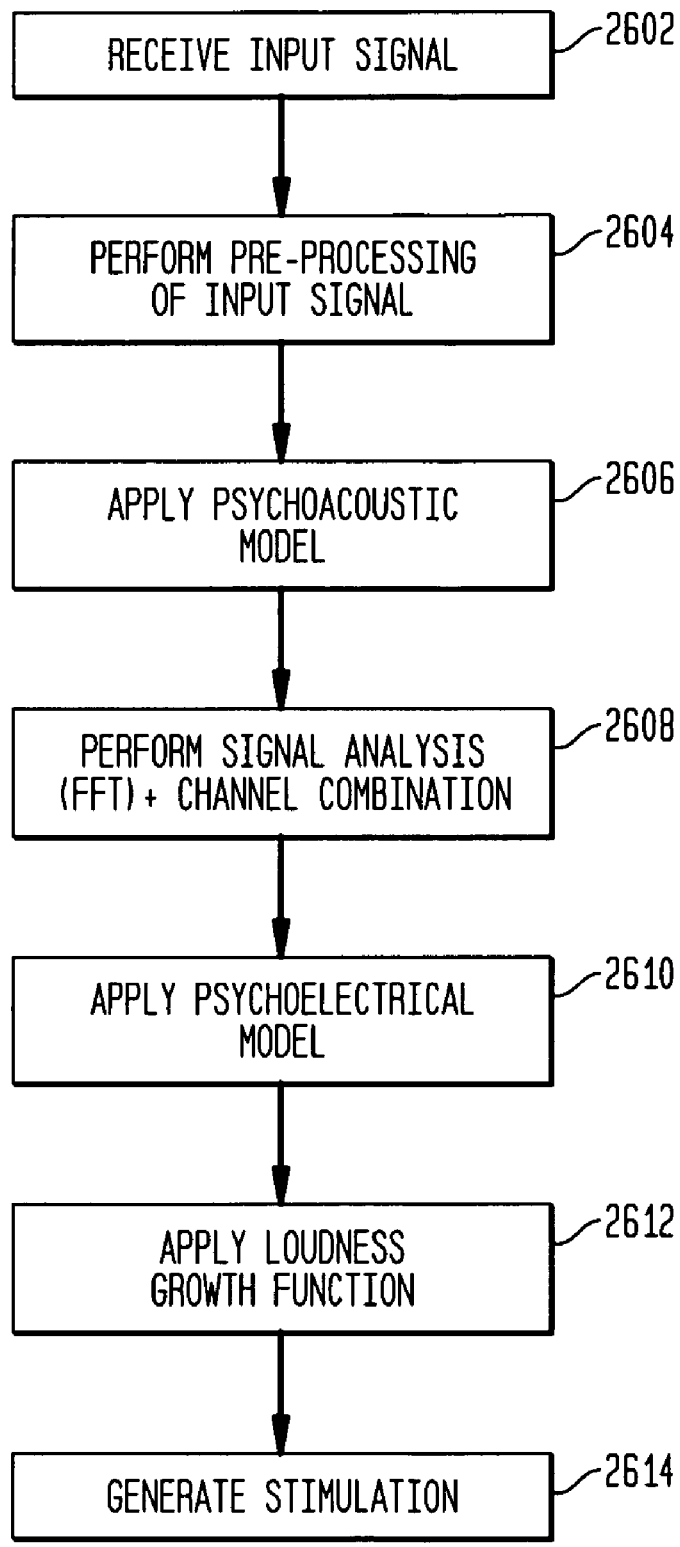
FIG. 26 illustrates an exemplary method for receiving and masking signals using both a psychoacoustic model and a psychoelectric model, in accordance with embodiments of the present invention.

FIG. 26 illustrates operations performed in one embodiment of the invention for receiving and masking signals using both a psychoacoustic model and a psychoelectric model. At block 2602, microphone 120 receives sounds which are converted to electrical signals. These signals may then undergo pre-processing at block 2604. This pre-processing, as with some of the above-discussed embodiments, may include using a pre-emphasis filter, automatic gain control (AGC), and/or manual sensitivity control (MSC), such as, for example, that used in the Advanced Combination Encoder (ACE) strategy.

Next, the signal is compressed using a psychoacoustic model. This model may, for example, be the MPEG1 Psychoacoustic Model 1, the MPEG1 Psychoacoustic Model 2, or, for example, any other psychoacoustic model now or later developed. Further, for example, the same or a similar strategy for applying the psychoacoustic model may be used as is commonly used in the MPEG Audio Layer-3 format (commonly referred to as MP3).

After psychoacoustic masking, the resulting signal then undergoes signal analysis at block 2608. For example, as discussed above with reference to block 906 of FIG. 9, this may include filtering the signals using a bank of band-pass filters to obtain a plurality of signals as is well-know to those of ordinary skill in the art. Moreover, in a cochlear prosthesis 100 where electrode array 134 includes 22 electrodes, the signal analysis may output 22 separate output signals, one corresponding to each electrode of electrode array 134. Additionally, in other embodiments, as discussed above, virtual channels may also be generated, thus resulting in possibly more than 22 output channels. Because, in this example, the psychoacoustic masking is applied prior to performing the signal analysis of block 2608, this method is referred to as a method employing forward processing of the psychoacoustic masking. The psychoacoustic masking of block 2606 may be determined in speech processing unit 116 of cochlear prosthesis 100.

The signal is then compressed using a psychoelectric model and stimulation signals selected for use by electrode array 134 at block 2610. The operations implemented to perform this step may be, for example, similar to the operations performed in connection with block 910 discussed above with reference to FIG. 9.

Alternatively, in another example, the signal analysis and channel combination block 2608 may select a number of maxima (i.e., stimulation signals) that block 2610 then analyzes to determine whether any of the received maxima would be masked, and therefore would be redundant. For example, in one embodiment, block 2610 may employ a masking check, such as discussed above, with reference to masking check 25 of FIG. 25. In such an example, a psychoelectric model may be used to generate masking table 26 of FIG. 25. This psychoelectric model may, for example, be a user-specific model determined using a method for determining a user-specific psychoelectric model, such as, for example, the above-described method of FIG. 2. Or, for example, the psychoelectric model may be a model for all cochlear prosthesis recipients or a subset of recipients for which the recipient is a member.

Further, in yet another example, rather than deleting signals that otherwise would be electrically masked for an implant recipient, the intensity of these signals may be increased so that they are perceived by the implant recipient. For example, application of the psychoacoustic model at block 2606 provides the frequencies that would be perceived by a normal hearing person. Some of these frequencies, however, may otherwise be masked in an implant due to stimulation of other electrodes of electrode array 134. Thus, in an embodiment, rather than deleting these signals that would otherwise be masked in an implant recipient, the signals are instead increased so that they are perceived by the implant recipient. This may be achieved by, for example, using a masking check and masking table, such as discussed with reference to FIG. 25 and increasing the amplitude of signals that otherwise would be masked so that they are perceived by the implant recipient. Further, the system may further use this masking table 26 to determine the precise intensity for the stimulation. For example, in a normal hearing person, the frequency that otherwise would be masked would be perceived in a normal hearing person at a certain intensity level. This information, in conjunction with the masking table 26 may be used to determine the intensity level for the signal so that it is perceived by the implant recipient at an intensity level approximating the intensity level for which a normal hearing individual would perceive the frequency.

After selection of the stimulation signals, a loudness growth function may be applied to the signals at block 2612 and the stimulation signals may be sent to electrode array 134 for stimulating auditory nerve 138 at block 2614, such as was discussed above with reference to blocks 910 and 912 of FIG. 9. As discussed above, these stimulation signals selected for stimulating auditory nerve 138 may be real channels (i.e., corresponding to a single electrode) and/or virtual channels involving, for example, the simultaneous or coordinated stimulation of multiple electrodes. Further, as with the embodiment of FIG. 9, the steps of blocks 2604 thru 2612 may be performed by speech processing unit 116 of cochlear prosthesis 100.

Figure 27:
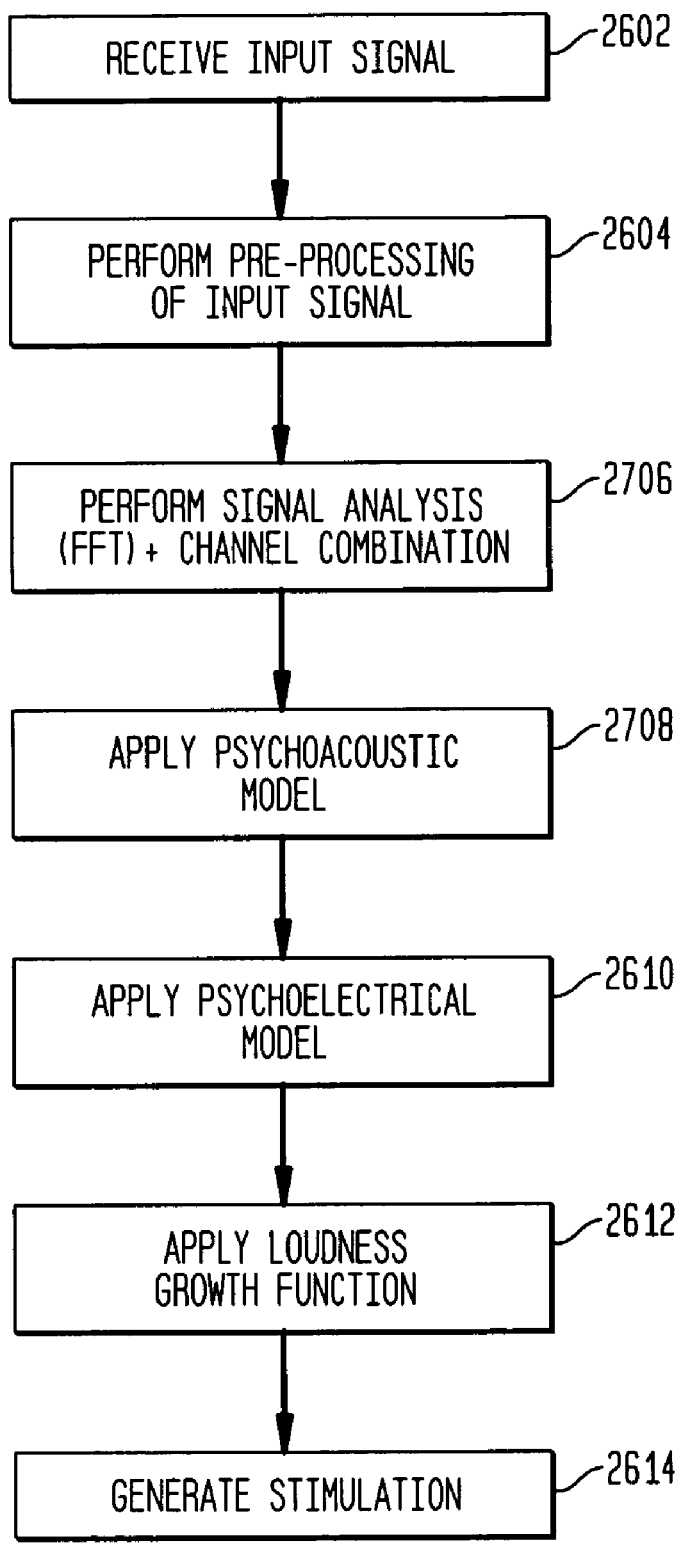
FIG. 27 illustrates an exemplary method for receiving and masking signals using both a psychoacoustic model and a psychoelectric model, in accordance with embodiments of the present invention.

FIG. 27 illustrates an exemplary method for receiving and masking signals using both a psychoacoustic model and a psychoelectric model, in accordance with methods and systems consistent with the invention. This exemplary method is identical to the above-discussed method of FIG. 26 with the exception that in this example the psychoacoustic model is applied after signal analysis (e.g., splitting the received signal into a plurality of stimulation signals corresponding to one or more of the electrodes of electrode array 134). Because in this example, the psychoacoustic model is applied after signal analysis block 2706, this method is referred to as a process employing backend processing of the psychoacoustic model. Further, in this example, the psychoacoustic model applied at block 2708 as with the above-discussed embodiments may be a model such as the MPEG1 Psychoacoustic Model 1 or Model 2, or may be a model for a group of people sharing a common characteristic with the implant recipient. Moreover, in this example, the psychoacoustic model may be applied using a method such as is commonly used for applying psychoacoustic models, such as the methodology employed by the MP3 format; or, for example a method such as the above discussed method described with reference to block 910 of FIG. 9 may be employed.

In the above description, the threshold in quite is applied to make app thresholds equal to the normal hearing threshold. It should be appreciated, however, that a new pre-filter may be used that emphasizes the frequencies that are most important to speech and that decreases the other frequencies. It this way important frequencies are more likely to be selected.

Although the above described embodiments were discussed with reference to a cochlear implant, in other embodiments these methods and systems may be used with other implant systems such as, for example, in an auditory brainstem implant or an electroacoustical device for a user.

All documents, patents, journal articles and other materials cited in the present application are hereby incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of providing neural stimulation to a recipient, comprising:
   receiving an acoustical signal;
   determining a set of stimulation signals based on the received acoustical signal, comprising:
      determining a first stimulation signal based on a perceptual power of the first stimulation signal; and
      determining at least one other stimulation signal based on a perceptual power of the at least one other stimulation signal using information indicative of a masking effect of the first stimulation signal on the at least one other stimulation signal; and
   applying stimuli to a recipient using the determined stimulation signals, wherein the acoustical signal is received and the set of stimulation signals are determined prior to application of the stimuli to the recipient using the determined stimulation signals.

2. The method of claim 1, wherein each determined stimulation signal corresponds to a set of one or more electrodes of an electrode array implanted in the recipient; and
   wherein the information indicative of the masking effect of the first stimulation signal on the at least one other stimulation signal comprises a strategy wherein stimulation signals corresponding to a set of one or more electrodes within a predetermined number of adjacent electrodes of the one or more electrodes corresponding to the first stimulation signal are excluded from being determined as the at least one other stimulation signal.

3. The method of claim 2, wherein the predetermined number is one.

4. The method of claim 1, wherein determining the set of stimulation signals further comprises:
   determining a first set of one or more signals using a psychoacoustic model indicative of a masking effect for a population of people; and
   determining the at least one other stimulation signal using at least one signal of the first set of one or more signals and information indicative of a masking effect derived from psychoelectric measurements.

5. The method of claim 1, further comprising:
   deriving the information indicative of the masking effect from a psychophysical model.

6. The method of claim 5, wherein the psychophysical model is a psychoacoustic model, and wherein the method further comprises:
   deriving the information indicative of the masking effect from the psychoacoustic model.

7. The method of claim 6, wherein the psychoacoustic model is selected from the set of the MPEG1 Psychoacoustic Model 1 and the MPEG1 Psychoacoustic Model 2.

8. The method of claim 5, wherein the psychophysical model is a psychoelectric model, and wherein the method further comprises:
  deriving the information indicative of the masking effect from the psychoelectric model.

9. The method of claim 8, wherein the psychoelectric model is a recipient-specific model determined based on measurements taken using an implant system implanted in the recipient.

10. The method of claim 5, wherein the psychophysical model is a psychoacoustic model, and wherein the method further comprises:
  deriving the information indicative of the masking effect from the psychoacoustic model.

11. The method of claim 10, wherein the psychoacoustic model is selected from the set of the MPEG1 Psychoacoustic Model 1 and the MPEG1 Psychoacoustic Model 2.

12. The method of claim 1, wherein applying stimuli to a recipient comprises:
  simultaneously applying stimuli to two or more electrodes of an electrode array.

13. A method of providing neural stimulation to a recipient, comprising:
  receiving an acoustic sound signal;
  determining a set of stimulation signals based on the received acoustic signal, comprising:
    determining a first stimulation signal based on a perceptual power of the first stimulation signal; and
    determining at least a second stimulation signal based on a perceptual power of the second stimulation signal using information indicative of a masking effect of the first stimulation signal on the second stimulation signal; and
    applying stimuli to a recipient using the first and second stimulation signals,
  wherein the acoustical signal is received and the set of stimulation signals are determined prior to application of the stimuli to the recipient using the determined stimulation signals.

14. The method of claim 13, wherein each of the first and second stimulation signals correspond to a set of one or more electrodes of an electrode array implanted in the recipient; and
  wherein the information indicative of the masking effect of the first stimulation signal on the second stimulation signal comprises a strategy wherein stimulation signals corresponding to a set of one or more electrodes within a predetermined number of adjacent electrodes of the one or more electrodes corresponding to the first stimulation signal are excluded from being determined as the at second stimulation signal.

15. The method of claim 14, wherein the predetermined number is one.

16. The method of claim 13, wherein determining the set of stimulation signals further comprises:
  determining a first set of one or more signals using a psychoacoustic model indicative of a masking effect for a population of people; and
  determining the at least second stimulation signal using at least one signal of the first set of one or more signals and information indicative of a masking effect derived from psychoelectric measurements.

17. The method of claim 13, further comprising:
  deriving the information indicative of the masking effect from a psychophysical model.

18. The method of claim 17, wherein the psychophysical model is a psychoelectric model, and wherein the method further comprises:
  deriving the information indicative of the masking effect from the psychoelectric model.

19. The method of claim 18, wherein the psychoelectric model is a recipient-specific model determined based on measurements taken using an implant system implanted in the recipient.

20. The method of claim 13, wherein applying stimuli to a recipient comprises:
  simultaneously applying stimuli to two or more electrodes of an electrode array.

* * * * *